US006551247B2

(12) United States Patent
Saito et al.

(10) Patent No.: US 6,551,247 B2
(45) Date of Patent: Apr. 22, 2003

(54) ULTRASONIC PROBE

(75) Inventors: Koetsu Saito, Nakano-Ku (JP); Yasushi Koishihara, Yokohama (JP); Junichi Takeda, Kawasaki (JP); Hirokazu Fukase, Kawasaki (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/777,670

(22) Filed: Feb. 7, 2001

(65) Prior Publication Data

US 2001/0021807 A1 Sep. 13, 2001

(30) Foreign Application Priority Data

Mar. 7, 2000 (JP) ....................................... 2000-061348
Mar. 28, 2000 (JP) ....................................... 2000-088675
Mar. 29, 2000 (JP) ....................................... 2000-090880
Mar. 30, 2000 (JP) ....................................... 2000-093313

(51) Int. Cl.[7] .................................................. A61B 8/14
(52) U.S. Cl. ....................... 600/459; 600/463; 310/334; 310/335; 310/322; 310/323
(58) Field of Search ................................ 600/459, 463; 310/322, 320, 334, 335, 323

(56) References Cited

U.S. PATENT DOCUMENTS 3,278,771 A 10/1966 Fry
4,217,684 A * 8/1980 Brisken et al. ............ 29/25.35
4,385,255 A * 5/1983 Yamaguchi et al. ........ 310/335
4,704,774 A * 11/1987 Fujii et al. ................. 29/25.35
5,163,436 A * 11/1992 Saitoh et al. ............... 600/459
5,410,204 A * 4/1995 Imabayashi et al. ... 310/323.13
5,495,137 A * 2/1996 Park et al. .................. 310/331
5,638,822 A * 6/1997 Seyed-Bolorforosh et al. .. 600/459
5,854,528 A * 12/1998 Nishikura et al. ..... 310/323.01
5,947,905 A * 9/1999 Hadjicostis et al. ........ 600/463
6,014,898 A * 1/2000 Finsterwald et al. .......... 73/642
6,117,083 A * 9/2000 Buck et al. ................. 600/459
6,123,673 A * 9/2000 Eberle et al. ............... 600/467

FOREIGN PATENT DOCUMENTS

DE 276 193 A1 2/1990
WO WO 97/03764 2/1997

* cited by examiner

*Primary Examiner*—Francis J. Jaworski
*Assistant Examiner*—William Jung
(74) *Attorney, Agent, or Firm*—Wenderoth, Lind & Ponack, L.L.P.

(57) ABSTRACT

Disclosed is an ultrasonic probe of high performance and high quality. The ultrasonic probe comprises a high molecular material having a conductive layer and is disposed between a piezoelectric element and an acoustic matching layer. The high molecular material has an acoustic impedance substantially equal to that of the acoustic matching layer. The ultrasonic probe thus configured can be formed into a slim shape which is easy to operate without degrading the performance thereof, such as sensitivity or frequency characteristics or the like. The ultrasonic probe is structured so as not to cause an electrical problem due to breakage of wire even if the piezoelectric element is cracked by a mechanical impact or the like, and thus a high quality ultrasonic probe can be provided, and noise can be reduced.

18 Claims, 11 Drawing Sheets

ULTRASONIC PROBE

FIELD OF THE INVENTION

The present invention relates to an ultrasonic probe to be used in an ultrasonic diagnostic apparatus or the like.

DESCRIPTION OF THE PRIOR ART

An ultrasonic probe is used, for example, in an ultrasonic diagnostic apparatus for a human body. One of the conventional ultrasonic probes is disclosed in Japanese Patent Laid-Open Publication No. Hei 8-122310. FIG. 17 shows a structure of this conventional ultrasonic probe. In FIG. 17, a piezoelectric element 31 is an element for transmitting and receiving an ultrasonic wave, and each face thereof is provided with an electrode. An acoustic matching layer 37 is made of conductive material and is provided on a face of one of the electrodes to efficiently transmit and receive an ultrasonic wave for a subject to be examined (human body). The ultrasonic probe further comprises a conductive layer 40 provided on a high molecular film 41 by deposition or other proper operations so as to be brought into contact with the acoustic matching layer 37. An acoustic lens 38 is provided on a face of the high molecular film to focus the ultrasonic wave. An FPC 34 is provided on the other electrode so as to form a conductive pattern, and a backing material 39 is provided on a face of the FPC 34. This structure allows an electrical connection to be maintained even if the piezoelectric element 31 is cracked by an external mechanical impact, and thereby provides a feature that the piezoelectric element is less likely to fail and stable quality is provided.

Referring to FIG. 17 more specifically, the piezoelectric element 31 is provided with a positive electrode 32 on one face thereof and with a ground electrode 33 on the other face thereof. Each of these electrodes 32, 33 is made of baked-silver formed by baking a composite of glass and silver, or of gold plating, sputtering or deposition, and has a thickness of 0.5 to 10 $\mu$m to provide a short pulse characteristic. The positive electrode 32 is provided, on a back face thereof, with a laminate of a positive electrode side conductive layer 35 and a positive electrode side base material layer 36 stacked in this order. The positive electrode side base material layer 36 is made of high molecular film or the like, and the positive electrode side conductive layer 35 is formed on this base material layer by plating, sputtering or deposition with metallic material such as copper or gold, or by fixing a metal foil thereto, and further is formed into a proper pattern, if necessary. Further, the backing material 39 is provided on a back face of the positive electrode side base material layer 36 so that a short pulse characteristic is achieved by braking the piezoelectric element 31.

Further, the acoustic matching layer 37 made of conductive material such as graphite is laminated on a front face of the ground electrode 33 (on the side of a subject to be examined), and a ground electrode side conductive layer 40 and a ground electrode side base material layer 41 are laminated on a front face of the acoustic matching layer 37.

The ground electrode side base material layer 41 is made of high molecular film or the like, and the ground electrode side conductive layer 40 is formed on this base material layer 41 by plating, sputtering or deposition with such metal as copper or gold, or by fixing a metallic foil thereto, where the ground electrode side conductive layer 40 is disposed below the base material layer 41 as shown in FIG. 17. Further, an acoustic lens 38 is provided on a front face of the ground electrode side base material layer 41 to focus the ultrasonic wave.

In this structure, a mechanical deformation is produced in the piezoelectric element 31 by an electric signal supplied between the positive electrode side conductive layer 35 and the ground electrode side conductive layer 40 from a main body of an ultrasonic diagnostic apparatus (not shown), and thereby an ultrasonic wave is transmitted.

The ultrasonic wave transmitted from this piezoelectric element 31, after the propagation efficiency thereof into a human body is enhanced by the acoustic matching layer 37 and the wave is focused by the acoustic lens 38, is transmitted into the human body (not shown). The ultrasonic wave transmitted into the human body produces a reflective wave when it is reflected by an interface of tissues in the human body. The reflective wave, after passing the same path as the transmitted ultrasonic wave in a reverse direction, is received by the piezoelectric element 31 and is transformed back into an electric signal to be sent as a received signal to the ultrasonic diagnostic apparatus. Based on this received signal, the ultrasonic diagnostic apparatus forms an image indicative of the information inside the human body to make a diagnosis. Another conventional ultrasonic probe is disclosed in Japanese Patent Laid-Open Publication No. Hei 11-276479.

FIG. 18 is a schematic perspective view of another conventional ultrasonic probe. In explaining this drawing, the word “up” means a direction from a lower part of the drawing to an upper part thereof. In FIG. 18, a piezoelectric element 51 is an element for transmitting and receiving an ultrasonic wave. A first electrode 53 and a second electrode 52 each being provided on one face of the piezoelectric element 51, respectively, are electrodes for applying a voltage to the piezoelectric element 51. The first electrode 53 works as a GND and forms a turning electrode which passes along a side face of the piezoelectric element extending parallel with a short axis direction thereof, and reaches a portion of a face of a backing material. The first electrode 53 of the piezoelectric element 51 is electrically connected to a copper foil 55, and the second electrode 52 is a signal electrode electrically connected to a flexible print circuit (FPC) 54 with a wiring pattern formed thereon. Each electrode is disposed on one of end faces of the piezoelectric element, respectively, in the short axis direction. Further, the piezoelectric element 51 and a plurality of acoustic matching layers are cut along a direction parallel with the short axis to form channel dividing grooves 56, so that a plurality of piezoelectric elements are arranged to align with the short axis direction.

A first acoustic matching layer 57*a* is provided on an upper face of the first electrode 53 (to face the subject to be examined) so that the ultrasonic wave may be efficiently transmitted and received thereby. A second acoustic matching layer 57*b* is provided on an upper face of the first acoustic matching layer 57*a* so that the ultrasonic wave may also be efficiently transmitted and received thereby. An acoustic lens 58 is provided on the second acoustic matching layer 57*b* to focus the ultrasonic wave. Further, a backing material 59 is provided on a lower face of the second electrode 52 in order to absorb undesired ultrasonic waves as well as to support the piezoelectric element 51.

In the conventional ultrasonic probe shown in FIG. 17; however, the high molecular film 41 is provided to be extended as an electrical terminal and is not contemplated as an acoustic matching layer. Accordingly, there occurs a problem in that the efficiency in transmitting and receiving the ultrasonic wave is reduced, and further the frequency characteristic is degraded. Further, there is another problem in that an insulator of a signal electrical terminal disposed between the piezoelectric element and the backing material is generally thick, which has a negative effect on the damping of the backing material and degrades the acoustic characteristic of the ultrasonic probe, especially the frequency characteristic thereof.

Further, in the conventional ultrasonic probe described above, the acoustic matching layer 37 is provided in order to efficiently propagate the ultrasonic wave transmitted from the piezoelectric element 31 (generally having a high acoustic impedance of about 25 to 35 Mrayl) into a human body (having an acoustic impedance of about 1.5 Mrayl), and the acoustic matching is optimized by adjusting the acoustic impedance and the thickness of the acoustic matching layer 37, and thereby the ultrasonic probe having waves of a short pulse length and high propagation efficiency is achieved. However, the acoustic matching is impaired and the pulse length and the propagation efficiency are degraded due to an existence of the ground electrode side conductive layer 40 made of metallic material between the acoustic matching layer 37 and the acoustic lens 38.

This problem is also seen at the positive electrode side conductive layer. The conductive layer has a greater adverse effect as the frequency of the ultrasonic wave increases.

The thickness of each conductive layer must be smaller than 5 $\mu$m in order to reduce the degradation in the pulse length and the propagation efficiency. On the other hand, however, the thinner conductive layer makes the electrical resistance (electrical impedance) larger, and thereby a driving electrical signal on an electrical conductive path is lowered to reduce the electrical signal applied to the piezoelectric element 1, and as a result, the electro-mechanical conversion efficiency from a viewpoint of the diagnostic apparatus is decreased.

Further, when the electrical impedance on the electrical conductive path is increased, the capability of removing external electrical noise is deteriorated, and accordingly, external electromagnetic noise causes the diagnosis image to be deteriorated, which makes the simultaneous optimization of an acoustic matching condition and an electrical conductive path more difficult, and also prevents an accurate diagnosis based on the ultrasonic image, which eventually might result in a serious problem of inducing a wrong diagnosis.

The present invention has been made to solve the problems described above, and an object thereof is, in an ultrasonic probe where progress toward higher resolution is being developed, to provide diagnostic information based on a highly accurate ultrasonic image by simultaneously optimizing the acoustic matching condition and the electrical conductive path.

Further, in the conventional system, since the electrodes are disposed on respective end faces of the piezoelectric element with respect to the short axis direction thereof, and are extended out therefrom, if the piezoelectric element is subjected to, for example, an external mechanical impact by a post-processing operation or the like, and thereby the first electrode fails to keep an electrical connection due to breakage thereof, the ability of transmitting and receiving the ultrasonic wave by the piezoelectric element is limited to only a portion of the electrode electrically connected to the copper foil or the FPC, and this sometimes causes to lower the performance of the piezoelectric element. Further, since the copper foil and the FPC are electrically connected by a conductive adhesive or the like at end faces of the piezoelectric element with respect to the short axis thereof, sometimes another problem results in that, when a conductive adhesive of high curing temperature is employed, an electrode is deteriorated by heat and thereby the performance of the piezoelectric element is lowered.

An ultrasonic probe of the present invention has been made to solve these problems. Another object of the present invention is to provide a high-quality piezoelectric probe, the performance of which is not degraded even if the piezoelectric element is cracked by a mechanical impact applied thereto.

The present invention has been made to solve the problems of the conventional system described above. A further object of the present invention is to provide a high-quality ultrasonic probe which has an acoustic impedance substantially equal to that of the acoustic matching layer, and does not deteriorate in performance, including sensitivity and frequency characteristics.

Further, in the conventional ultrasonic probe described above, there is another problem that an insulator of the signal electrical terminal disposed between the piezoelectric element and the backing material is generally thick, which has a negative effect on the damping performance of the backing material, and degrades the acoustic characteristic of the ultrasonic probe, especially the frequency characteristic thereof.

The present invention has been made to solve these problems, and a still further object of the present invention is to provide an ultrasonic probe which does not deteriorate the acoustic characteristic, especially of the frequency characteristic.

SUMMARY OF THE INVENTION

In order to solve the problems described above, the present invention provides an ultrasonic probe in which a high molecular material layer including a conductive layer is disposed on a piezoelectric element, and an acoustic matching layer is disposed on the high molecular material layer, wherein the high molecular material layer has an acoustic impedance substantially equal to that of the acoustic matching layer and the total thickness of these two layers is substantially equal to a quarter wavelength of an ultrasonic wave.

In an alternative ultrasonic probe of the present invention, a high molecular material layer including a conductive layer is disposed on a first acoustic matching layer, and a second acoustic matching layer is disposed on the high molecular material layer, wherein the high molecular material layer has an acoustic impedance substantially equal to that of the second acoustic matching layer and the total thickness of these two layers is substantially equal to a quarter wavelength of an ultrasonic wave.

In another alternative ultrasonic probe of the present invention, a conductive layer electrically connected to an electrode face of a piezoelectric element is disposed between the electrode face of the piezoelectric element and an acoustic matching layer, and a high molecular material layer including a conductive layer formed thereon is disposed on the acoustic matching layer side, wherein the high molecular material layer has an acoustic impedance substantially equal to that of the acoustic matching layer and the total thickness of these two layers is substantially equal to a quarter wavelength of an ultrasonic wave.

In a further alternative ultrasonic probe of the present invention, a high molecular material layer is disposed between a first acoustic matching layer and a second acoustic matching layer located on a subject side, wherein an acoustic impedance of the high molecular material layer is between that of the first acoustic matching layer and that of the second acoustic matching layer, or is substantially equal to that of said first acoustic matching layer or that of the second acoustic matching layer.

Because of these structures described above, the sensitivity of transmitting and receiving the ultrasonic wave can be improved and further, desired frequency characteristics can be provided. Accordingly, an ultrasonic diagnostic apparatus with an image of higher resolution and higher sensitivity can be provided, and also an ultrasonic probe which is less likely to fail and has a stable quality can be obtained since an electrical connection can be maintained even if the piezoelectric element is cracked by an external mechanical impact.

A still further alternative ultrasonic probe of the present invention includes a high molecular material layer disposed on a piezoelectric element and an acoustic matching layer disposed on the high molecular material layer. The high molecular material layer comprises a base material made of high molecular material, and a conductive layer made of conductive material is formed thereon, wherein the high molecular material layer has an acoustic impedance substantially equal to that of the acoustic matching layer. Accordingly, the sensitivity of transmitting and receiving an ultrasonic wave can be improved and desired frequency characteristics can be provided. Thus, an ultrasonic diagnostic apparatus with an image of higher resolution and higher sensitivity can be provided, and also an ultrasonic probe which is less likely to fail and has a stable quality can be obtained since an electrical connection can be maintained even if the piezoelectric element is cracked by an external mechanical impact.

Further, a yet another alternative ultrasonic probe of the present invention includes a high molecular material layer disposed on a piezoelectric element and an acoustic matching layer disposed on the high molecular material layer. The high molecular material layer comprises a base material made of high molecular material, and a conductive layer made of conductive material is formed thereon. The high molecular material layer has an acoustic impedance substantially equal to that of the acoustic matching layer and the total thickness of these two layers is substantially equal to a quarter wavelength of the ultrasonic wave, and thereby the sensitivity of transmitting and receiving the ultrasonic wave can be improved and further desired frequency characteristics can be provided. Accordingly, an ultrasonic diagnostic apparatus with an image of higher resolution and higher sensitivity can be provided, and also an ultrasonic probe which is less likely to fail and has a stable quality can be obtained since an electrical connection can be maintained even if the piezoelectric element is cracked by an external mechanical impact.

Further, an additional alternative ultrasonic probe of the present invention includes a high molecular material layer disposed on a piezoelectric element and an acoustic matching layer disposed on the high molecular material layer. The high molecular material layer comprises a base material made of high molecular material, and a conductive layer made of conductive material is formed thereon. The high molecular material is made of polyimide, polyethylene-terephthalate, polysulphon, polycarbonate, polyester, polystyrene, poly-phenylene-sulphide or the like, and the high molecular material layer has an acoustic impedance substantially equal to that of the acoustic matching layer, and thereby the sensitivity of transmitting and receiving the ultrasonic wave can be improved and further desired frequency characteristics can be provided. Accordingly, an ultrasonic diagnostic apparatus with an image of higher resolution and higher sensitivity can be provided, and also an ultrasonic probe which is less likely to fail and has a stable quality can be obtained since an electrical connection can be maintained even if the piezoelectric element is cracked by an external mechanical impact.

Further, another alternative ultrasonic probe of the present invention includes a high molecular material layer disposed on a first acoustic matching layer and a second acoustic matching layer disposed on the high molecular material layer. The high molecular material layer comprises a base material made of high molecular material, and a conductive layer made of conductive material is formed thereon, wherein the high molecular material layer has an acoustic impedance substantially equal to that of the second acoustic matching layer, and thereby the sensitivity of transmitting and receiving the ultrasonic wave can be improved and further desired frequency characteristics can be provided. Accordingly, an ultrasonic diagnostic apparatus with an image of higher resolution and higher sensitivity can be provided, and also an ultrasonic probe which is less likely to fail and has a stable quality can be obtained since an electrical connection can be maintained even if the piezoelectric element is cracked by an external mechanical impact.

Further, another alternative ultrasonic probe of the present invention includes a high molecular material layer disposed on a first acoustic matching layer and a second acoustic matching layer disposed on the high molecular material layer. The high molecular material layer comprises a base material made of high molecular material, and a conductive layer made of conductive material is formed thereon. The high molecular material layer has an acoustic impedance substantially equal to that of the second acoustic matching layer, and the total thickness of these two layers is substantially equal to a quarter wavelength of the ultrasonic wave, and thereby the sensitivity of transmitting and receiving the ultrasonic wave can be improved and further desired frequency characteristics can be provided. Accordingly, an ultrasonic diagnostic apparatus with an image of higher resolution and higher sensitivity can be provided, and also an ultrasonic probe which is less likely to fail and has a stable quality can be obtained since an electrical connection can be maintained even if the piezoelectric element is cracked by an external mechanical impact.

Further, another alternative ultrasonic probe of the present invention includes a high molecular material layer disposed on a first acoustic matching layer and a second acoustic matching layer disposed on the high molecular material layer. The high molecular material layer comprises a base material made of high molecular material, and a conductive layer made of conductive material is formed thereon. The high molecular material is made of polyimide, polyethylene-terephthalate, polysulphon, poly-carbonate, polyester, polystyrene, poly-phenylene-sulphide or the like, and the high molecular material layer has an acoustic impedance substantially equal to that of the said second acoustic matching layer, and thereby the sensitivity of transmitting and receiving the ultrasonic wave can be improved and further desired frequency characteristics can be provided. Accordingly, an ultrasonic diagnostic apparatus with an image of higher resolution and higher sensitivity can be provided, and also an ultrasonic probe which is less likely to fail and has a stable quality can be obtained since an electrical connection can be maintained even if the piezoelectric element is cracked by an external mechanical impact.

Further, another alternative ultrasonic probe of the present invention includes a first conductive layer which is made of conductive material and is disposed between an electrode face of a piezoelectric element and an acoustic matching layer so as to be electrically connected to the electrode face of the piezoelectric element. A high molecular material layer is disposed on the acoustic matching layer side. The high molecular material layer comprises a base material made of high molecular material, and a second conductive layer made of conductive material is formed thereon. The high molecular material layer has an acoustic impedance substantially equal to that of the acoustic matching layer, and thereby the sensitivity of transmitting and receiving the ultrasonic wave can be improved and further desired frequency characteristics can be provided. Accordingly, an image on an ultrasonic diagnostic apparatus may be improved to be of higher resolution and of higher sensitivity, and further noise can be reduced since the conductive material works as a shield.

Further, another alternative ultrasonic probe of the present invention includes a conductive layer which is made of conductive material and is disposed between an electrode face of a piezoelectric element and an acoustic matching layer so as to be electrically connected to the electrode face of the piezoelectric element. A high molecular material layer is disposed on the acoustic matching layer side. The high molecular material layer comprises a base material made of high molecular material, and a conductive layer made of conductive material is formed thereon. The high molecular material layer has an acoustic impedance substantially equal to that of the acoustic matching layer, and thereby the sensitivity of transmitting and receiving the ultrasonic wave can be improved and further desired frequency characteristics can be provided. Accordingly, an image of an ultrasonic diagnostic apparatus may be improved to be of higher resolution and of higher sensitivity, and further noise can be reduced since the conductive material works as a shield.

Further, another alternative ultrasonic probe of the present invention includes a first acoustic matching layer located on a piezoelectric element side, a second acoustic matching layer located on a subject side, and a high molecular material layer between the first acoustic matching layer and the second acoustic matching layer. The high molecular material layer comprises a base material made of high molecular material, and a conductive layer made of conductive material is formed thereon, wherein an acoustic impedance of the high molecular material layer is between those of the first acoustic matching layer and said second acoustic matching layer, or substantially equal to that of the first acoustic matching layer or the second acoustic matching layer, and thereby the sensitivity of transmitting and receiving the ultrasonic wave can be improved and further desired frequency characteristic can be provided. Accordingly, an ultrasonic diagnostic apparatus with an image of higher resolution and higher sensitivity can be provided, and also an ultrasonic probe which is less likely to fail and has a stable quality can be provided since an electrical connection can be maintained even if the piezoelectric element is cracked by an external mechanical impact.

Further, another alternative ultrasonic probe of the present invention comprises a piezoelectric element having electrodes on both sides thereof, a backing material on one electrode side of the piezoelectric element, and a signal electrical terminal between the piezoelectric element and the backing material. The signal electrical terminal comprises an insulator facing the backing material and a conductive material facing one electrode face of the piezoelectric element so as to be electrically connected to the piezoelectric element. The insulator of the signal electrical terminal has a thickness equal to or less than $1/25$ wavelength of an ultrasonic wave at an area facing an ultrasonic wave emitting surface of the piezoelectric element.

Because of the structure described above, there can be provided an ultrasonic probe having an improved sensitivity for transmitting and receiving the ultrasonic wave, a higher resolution and further, an improved frequency characteristic. Accordingly, an ultrasonic diagnostic apparatus with an image of higher resolution and higher sensitivity can be provided, and also an ultrasonic probe which is less likely to fail and has a stable quality can be provided since an electrical connection can be maintained even if the piezoelectric element is cracked by an external mechanical impact.

Further, another ultrasonic probe of the present invention has an insulating material made of material selected from a group consisting of polyimide, polyethylene-terephthalate, poly-sulphon, poly-carbonate, polyester, polystyrene, and poly-phenylene-sulphide.

An ultrasonic probe of the present invention has a feature in that an acoustic impedance of an insulator is less than those of the piezoelectric element and the backing material.

In another aspect of the present invention, an ultrasonic probe comprises a piezoelectric element having electrodes on both sides thereof, a backing material on one electrode side of the piezoelectric element, and a first signal electrical terminal between the piezoelectric element and the backing material. The first signal electrical terminal comprises an insulator facing the backing material and a conductive material facing one electrode face of the piezoelectric element so as to be electrically connected to the piezoelectric element. An insulator of the first signal electrical terminal has a thickness equal to or less than $1/25$ wavelength of an ultrasonic wave at an area facing an ultrasonic wave emitting surface of the piezoelectric element. A second signal electrical terminal is disposed on a lateral outer side of the backing material. The second signal electrical terminal comprises an insulator and a conductive material. The conductive material of the first signal electrical terminal and the conductive material of the second signal electrical terminal are electrically connected to each other.

Because of the structure described above, there can be provided an ultrasonic probe having an improved sensitivity for transmitting and receiving the ultrasonic wave, a higher resolution and further, an improved frequency characteristic. Accordingly, an ultrasonic diagnostic apparatus with an image of higher resolution and higher sensitivity can be provided, and also an ultrasonic probe which is less likely to fail and has a stable quality can be provided since an electrical connection can be maintained even if the piezoelectric element is cracked by an external mechanical impact. Further, another advantage is that the ultrasonic probe can be easily manufactured.

Further, according to another feature of an ultrasonic probe of the present invention, an area of a conductive layer covering an electrode portion of a piezoelectric element has different thicknesses from one area thereof to another area thereof so that the thickness of the conductive layer may be optimized in respective areas from an acoustic viewpoint as well as an electrical conductive path viewpoint.

That is, there may be provided an ultrasonic probe comprising a piezoelectric element having a positive electrode on one face thereof and having a ground electrode another face thereof, and a conductive layer laminated so as to partially overlap at least one of the electrodes, wherein the thickness of the conductive layer in an acoustic effective area is smaller than that in an area at the outside of the acoustic effective area.

According to the structure described above, the area of the conductive layer overlapping the one of the electrodes (acoustic effective area) may be made thin so that an acoustical negative effect can be reduced, and in the other area the conductive layer is used as an electrically conductive path may be made thick so that the electrical impedance can be reduced. By this structure, both the acoustic matching condition and the electrical conductive path can be optimized simultaneously.

In addition to the similar operation and effect described above, the structure including the conductive layer formed on a base material has remarkable advantage in that the conductive portion formed by the thinner portion of the conductive layer is not likely to be creased, crinkled or eventually plastically deformed, which makes it easy to handle the conductive layer and the ultrasonic probe during the production process thereof.

Further, another ultrasonic probe of the present invention comprises a piezoelectric element having a positive electrode on one face thereof and having a ground electrode on another face thereof, an acoustic matching layer on a front face of the ground electrode, a base material layer on a front face of the acoustic matching layer, and a conductive layer disposed on the base material layer. A portion of the conductive layer, at least in an acoustic effective area, is thinner than that of an area outside of the acoustic effective area. By this structure, in addition to the similar operation and effect described above, there may be provided another advantageous effect in that the base material layer works as a second acoustic matching layer.

Further, another alternative ultrasonic probe of the present invention comprises a piezoelectric element having electrodes on both sides thereof, an acoustic matching layer contacting one electrode face of the piezoelectric element, and a backing material disposed on the other side of the piezoelectric element. The acoustic matching layer is made of conductive material and is electrically connected to the one electrode face of the piezoelectric element, and an end portion of the acoustic matching layer is electrically connected to a conductive film disposed on a side portion of the backing material. Thereby, the one electrode face of the piezoelectric element is extended out to the conductive film.

This structure allows a curved face to be easily formed after a cutting machining operation, and further allows an electrical connection to be maintained through the conductive acoustic matching layer even if the piezoelectric element is cracked by an external mechanical impact or the like, and thereby the performance of the piezoelectric element is not degraded and is less likely to fail, whereby the quality thereof can be stabilized.

Further, there may be provided an ultrasonic probe which can be easily manufactured without degrading the performance thereof since the piezoelectric element need not be exposed to a hot environment.

Further, an alternative ultrasonic probe of the present invention has an acoustic matching layer made of graphite.

Further, another alternative ultrasonic probe of the present invention has an insulating layer provided in a space between an acoustic matching layer, extended out from a piezoelectric element, and a backing material.

This structure allows the insulating layer to support the acoustic matching layer and also reinforces the strength of the acoustic matching layer against a mechanical impact applied during a machining process, which facilitates manufacturing of the ultrasonic probe.

Further, another alternative ultrasonic probe of the present invention has an insulating layer made of material selected from the group consisting of ceramic, acrylic resin, plastic, epoxy resin, cyanoacrylate and urethane resin.

Further, another alternative ultrasonic probe of the present invention comprises a piezoelectric element having electrodes on both sides thereof, a first acoustic matching layer contacting one of the electrodes, a second acoustic matching layer on an opposite side of the first acoustic matching layer with respect to the piezoelectric element, and a backing material disposed on the other side of the piezoelectric element. The first acoustic matching layer is made of conductive material and is electrically connected to the one electrode, and an end portion of the first acoustic matching layer is electrically connected to a conductive film disposed on a side portion of the backing material so that the one electrode may be extended to the conductive film.

This structure allows a curved face to be easily formed after a cutting machining operation, and further allows an electrical connection to be maintained through the conductive acoustic matching layer even if the piezoelectric element is cracked by an external mechanical impact or the like, and thereby the performance of the piezoelectric element is not degraded and is less likely to fail, whereby a stable quality can be obtained.

Further, an alternative ultrasonic probe of the present invention includes a second acoustic matching layer having a conductive layer electrically connected to the first acoustic matching layer.

This structure allows an electrical connection to be maintained even if the piezoelectric element and the first acoustic matching layer are cracked by an external mechanical impact, and thereby the ultrasonic probe is less likely to fail and a stable quality can be obtained.

Further, an alternative piezoelectric probe of the present invention includes a second acoustic matching layer made of material selected from the group consisting of polyimide, polyethylene-terephthalate, polysulphon, polycarbonate, polyester, polystyrene, and poly-phenylene-sulphide.

DESCRIPTION OF THE PREFERRED EMBODIMENTS OF THE PRESENT INVENTION

Preferred embodiments of the present invention will be described in detail with reference to the attached drawings.

Figure 1:
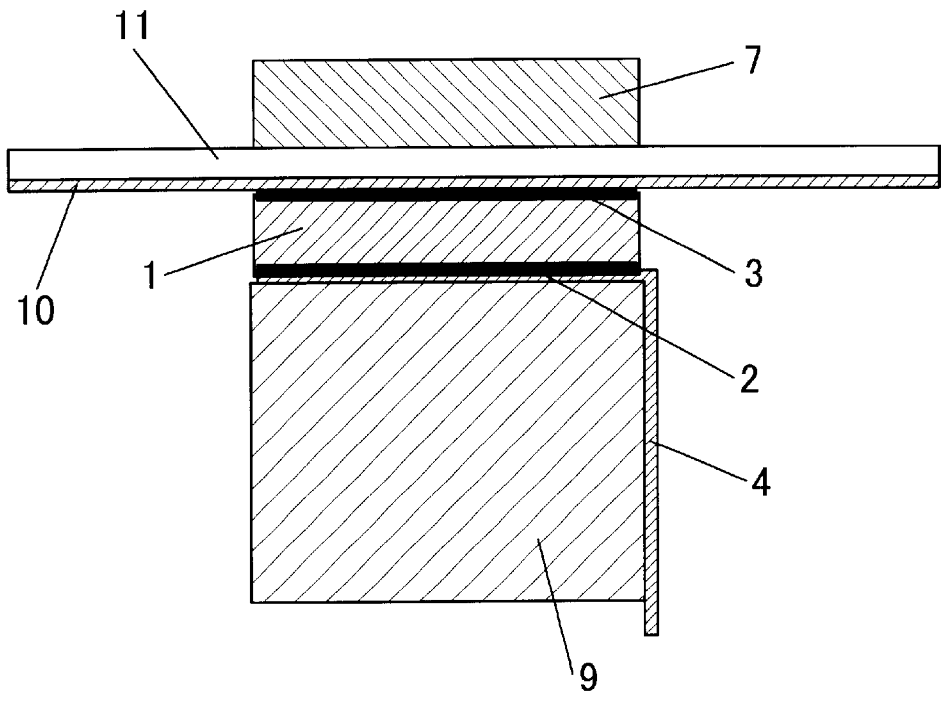
FIG. 1 is a schematic cross sectional view of an ultrasonic probe of a first embodiment according to the present invention.

FIG. 1 is a schematic cross sectional view of an ultrasonic probe of a first embodiment according to the present invention.

Referring to FIG. 1, the piezoelectric probe of the present invention comprises: a piezoelectric element 1 for transmitting and receiving a ultrasonic wave, which is made of a piezoelectric ceramic including PZT-based material, single crystal or high molecular material such as PVDF (polyvinylidene fluoride); a ground electrode 3 formed on one surface of the piezoelectric element by depositing or sputtering gold or silver thereon, or by baking silver thereon; a positive electrode 2 formed on the other surface of the piezoelectric element by depositing or sputtering gold or silver thereon, or by baking silver thereon, same as with the ground electrode 3; a signal electrical terminal 4 extended from the positive electrode 2; a backing material 9 for mechanically holding the piezoelectric element 1 and for functioning to dampen undesired ultrasonic signals; a high molecular material layer 11 having high molecular material as a base material and being provided on the ground electrode 3; a conductive layer 10 made of conductive material and provided on a surface of the high molecular material layer 11 facing the piezoelectric element 1 by deposition, sputtering, or plating with copper, nickel, silver, gold or the like so as to be electrically connected to the ground electrode 3 provided on the piezoelectric element 1; and an acoustic matching layer 7 provided on another surface of the high molecular material layer 11. Further, an acoustic lens for focusing an ultrasonic beam and for being brought into contact with a subject to be examined is sometimes provided on the acoustic matching layer 7 (not shown).

This ultrasonic probe transmits and receives the ultrasonic wave by applying an electrical signal from a main body of an ultrasonic diagnostic apparatus through the signal electrical terminal 4 and the conductive layer 10 or GND (ground terminal) to the piezoelectric element 1, and thereby inducing the piezoelectric element 1 to be vibrated mechanically. An ultrasonic probe of an ultrasonic diagnostic apparatus for diagnosing a human body as a subject to be examined is a so-called sensor used for diagnosing the human body, which is brought into direct contact with the human body, transmits the ultrasonic wave into the human body, and receives a wave reflected from the human body, so that the signal of the reflected wave is processed at the main body of the apparatus and an image for diagnosis is displayed on a monitor.

The ground electrode 3 provided on the piezoelectric element 1, and the conductive layer 10 provided on the high molecular material layer 11, are electrically connected to each other by a method using a conductive adhesive or a so-called ohmic contact method using a very thin epoxy resin layer.

The high molecular material layer 11 having the conductive layer 10 formed thereon, though illustrated as being laterally extended in FIG. 1, is eventually folded along a side face of the backing material 9 to be made slim as a whole so as to facilitate an easy operation. Accordingly, the high molecular material layer 11 with the conductive layer 10 formed thereon shall be made thinner because, if it is thick, it cannot be folded exactly along the side face of the backing material 9 so as to provide a slim shape as a whole. As a result of actual experimentation using polyimide as the high molecular material layer 11, it was found that an upper limit of the thickness was 0.05 mm, and in the case of a thickness of more than 0.05 mm, it was difficult to fold the high molecular material layer exactly along the side face of the backing material 9 to provide a slim shape as a whole, because of blistering or bonding separation generated between the ground electrode 3 and the conductive layer 10. Therefore, the thickness of the high molecular material layer 11 should be less than 0.05 mm. This high molecular material layer 11 should not degrade the performance of transmitting and receiving the ultrasonic wave, and is preferably as thin as possible so as not to substantially affect this performance. The present embodiment has a feature in that this high molecular layer 11 is designed to perform the same function as the acoustic matching layer 7. That is, the materials of the high molecular material layer 11 and the acoustic matching layer 7 are selected so as to have substantially the same acoustic impedance and the total thickness of the high molecular material layer 11, and the acoustic matching layer 7 is adjusted to be about a quarter wavelength of the setting frequency, so that the high molecular material layer 11 can function as a kind of acoustic matching layer without affecting or degrading the performance of transmitting and receiving the ultrasonic wave or sensitivity and frequency characteristics.

Preferable materials used as the high molecular material layer 11 are polyimide, polyethylene-terephthalate, polysulphon, polycarbonate, polyester, polystyrene, polyphenylene-sulphide and the like. The acoustic impedance of these materials is within the range of 3 to 4 to MRayl. As for the acoustic matching layer 7, the same materials as that of the high molecular material layer 11 may be employed, and also other materials may be employed, which are close to the materials of the high molecular material layer in terms of acoustic impedance. These materials are, for example, epoxy resin or polyurethane resin having an acoustic impedance of 2.5 to 1 Mrayl. In the case of an ultrasonic probe having a setting frequency of 3.5 MHz, for example, if the polyimide (acoustic velocity=2200 m/sec) with a thickness of 0.05 mm is used as the high molecular material layer 11 and epoxy resin (acoustic velocity=2500 m/sec) is employed as the acoustic matching layer 7, the thickness of polyimide, i.e. 0.05 mm, at a frequency of 3.5 MHz is equal to 1/12.25 wavelength (0.08 wavelength). Thus, the thickness of the epoxy resin should be 1/5.88 wavelength (0.17 wavelength) or 0.121 mm, and the total thickness of the high molecular material layer 11 of polyimide and the acoustic matching layer 7 of epoxy resin should be adjusted to a quarter wavelength (0.25 wavelength).

On the other hand, the conductive layer 10 formed on the high molecular material layer 11 causes no problem at all since the thickness thereof is a few μm, and thus it hardly affects the performance thereof.

As described above, the piezoelectric element of the first embodiment of the present invention can be formed into a slim shape which is easy to operate without degrading performance. Further, an ultrasonic probe of high quality can be provided since the structure thereof causes no electrical problem due to a breakage of wire even if the piezoelectric element is cracked by a mechanical impact or the like.

Figure 2:
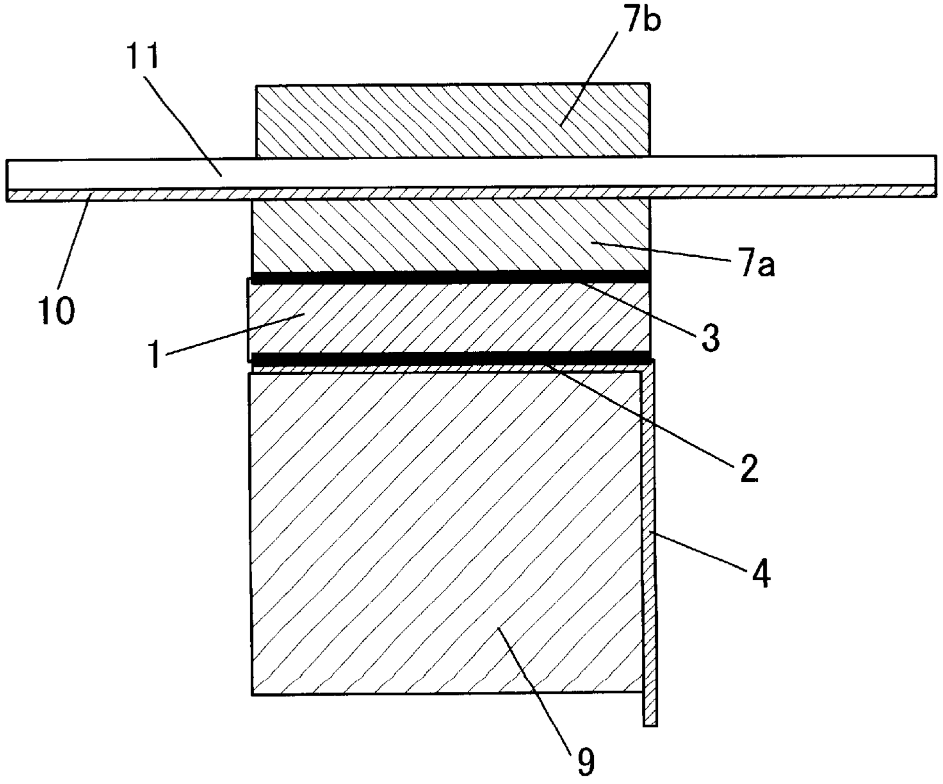
FIG. 2 is a schematic cross sectional view of an ultrasonic probe of a second embodiment according to the present invention.

FIG. 2 is a schematic cross sectional view of an ultrasonic probe of a second embodiment according to the present invention.

The second embodiment of the present invention is an ultrasonic probe in which a high molecular material layer having a conductive layer formed thereon is a first acoustic matching layer provided on one electrode surface of a piezoelectric element, and a second acoustic matching layer for the conductive layer to be electrically connected to the first acoustic matching layer, wherein the acoustic impedance of the high molecular material layer is substantially equal to that of the second acoustic matching layer. The second embodiment provides a high quality ultrasonic probe which allows an electrical terminal to be easily extended from an electrode of the piezoelectric element, and also allows good sensitivity and frequency characteristics in transmitting and receiving an ultrasonic wave to be secured because the high molecular material also serves as a part of the acoustic matching layer. The second embodiment further prevents a possible fault caused by a breakage of wire even if the piezoelectric element is cracked by a mechanical impact or the like.

Referring to FIG. 2, reference numerals 1 to 11 are similar to those of the first embodiment in FIG. 1. That is, the ultrasonic probe of the second embodiment of the present invention has a piezoelectric element 1, a ground electrode 3, a positive electrode 2, a signal electrical terminal 4, a backing material 9, a high molecular material layer 11, and a conductive layer 10. Further, the ultrasonic probe of the present embodiment has a first acoustic matching layer **7*a* provided on a piezoelectric element side, and a second acoustic matching layer 7*b* provided on the high molecular material layer 11. The first acoustic matching layer 7*a* and the second acoustic matching layer 7*b* are provided to improve the efficiency of transmitting and receiving the ultrasonic wave by the piezoelectric element 1, and in this second embodiment, this first acoustic matching layer 7*a* is made of conductive material configured to be electrically connected to the positive electrode 2 of the piezoelectric element by a bonding method such as ohmic contact or the like. Generally, material such as graphite is used as the first acoustic matching layer 7*a*, but in an alternative method, the first acoustic matching layer 7*a* may be made of insulating material if it is provided with a conductive layer by performing a certain method such as deposition or plating so as to be electrically connected to the ground electrode 3. Then, the high molecular material layer 11 having the conductive layer 10 formed thereon is bonded onto a surface of the first acoustic matching layer 7*a* by performing a bonding method such as ohmic contact so that the conductive layer 10 is brought into contact with the surface of the first acoustic matching layer 7*a*, and thereby the high molecular material layer 11 is electrically connected through the first acoustic matching layer 7*a* to the ground electrode 3. Further, the second acoustic matching layer 7*b* is provided on another surface of the high molecular material layer 11 by performing a bonding or injection operation or the like. Further, an acoustic lens for focusing an ultrasonic beam and for being brought into contact with a subject to be examined is sometimes provided on the acoustic matching layer 7** (not shown).

In the second embodiment, the high molecular material layer 11 is designed so as to perform a similar function as that of the second acoustic matching layer **7*b*, as in the first embodiment. That is, the materials of the high molecular material layer 11 and the second acoustic matching layer 7*b* are selected so as to have nearly the same acoustic impedance, and the total thickness of the high molecular material layer 11 and the second acoustic matching layer 7*b* is adjusted to be about a quarter wavelength of the ultrasonic wave at the setting frequency, so that the high molecular material layer 11** may not affect or degrade the performance of transmitting and receiving the ultrasonic wave or the sensitivity and frequency characteristics.

Preferable materials used as the high molecular material layer 11 are polyimide, polyethylene-terephthalate, polysulphon, polycarbonate, polyester, polystyrene, polyphenylene-sulphide and the like. The acoustic impedance of these materials is within the range of 3 to 4 MRayl. As for the second acoustic matching layer **7*b*, the same materials as that of the high molecular material layer 11 may be employed, and also other materials may be employed which have a similar acoustic impedance, such as epoxy resin or polyurethane resin having an acoustic impedance of 2.5 to 4 MRayl. In the case of an ultrasonic probe having a setting frequency of 3.5 MHz, for example, if the polyimide (acoustic velocity=2200 m/sec) with a thickness of 0.05 mm is used as the high molecular material layer 11, and epoxy resin (acoustic velocity=2500 m/sec) is employed as the second acoustic matching layer 7*b*, the polyimide thickness of 0.05 mm at the frequency of 3.5 MHz is equal to 1/12.5 wavelength (0.08 wavelength). Thus, the thickness of the epoxy resin should be 1/5.88 wavelength (0.17 wavelength) or 0.121 mm, and the total thickness of the high molecular material layer 11 of polyimide and the second acoustic matching layer 7*b*** of epoxy resin should be adjusted to a quarter wavelength (0.25 wavelength).

On the other hand, the conductive layer 10 formed on the high molecular material layer 11 causes no problem at all since the thickness thereof is a few μm, and thus it hardly affects the performance thereof.

Though in the second embodiment, the material employed as the high molecular material layer 11 and that employed as the second acoustic matching layer **7*b* are similar in their acoustic impedance, a similar effect can also be obtained in other cases where the material employed as the high molecular material layer 11 has an acoustic impedance between those of the first acoustic matching layer 7*a* and the second acoustic matching layer 7***b*, or has another acoustic impedance substantially equal to that of the first acoustic matching layer 7*a*.

Though in the second embodiment, a case where the material employed as the high molecular material layer 11 and that employed as the second acoustic matching layer 7*b* are similar in their acoustic impedance is described, a similar effect can also be obtained in other cases where the material employed as the high molecular material layer 11 has an acoustic impedance substantially equal to that of the first acoustic matching layer 7*a* and the total thickness of the first acoustic matching layer 7*a* and the high molecular material layer 11 is adjusted to be about a quarter wavelength.

As described above, the piezoelectric element according to the second embodiment can be formed into a slim shape and be easy to operate without degrading performance and the sensitivity and frequency characteristics. Further, an ultrasonic probe of high quality can be provided since the structure thereof causes no electrical problem due to a breakage of wire even if the piezoelectric element is cracked by a mechanical impact or the like.

Figure 3:
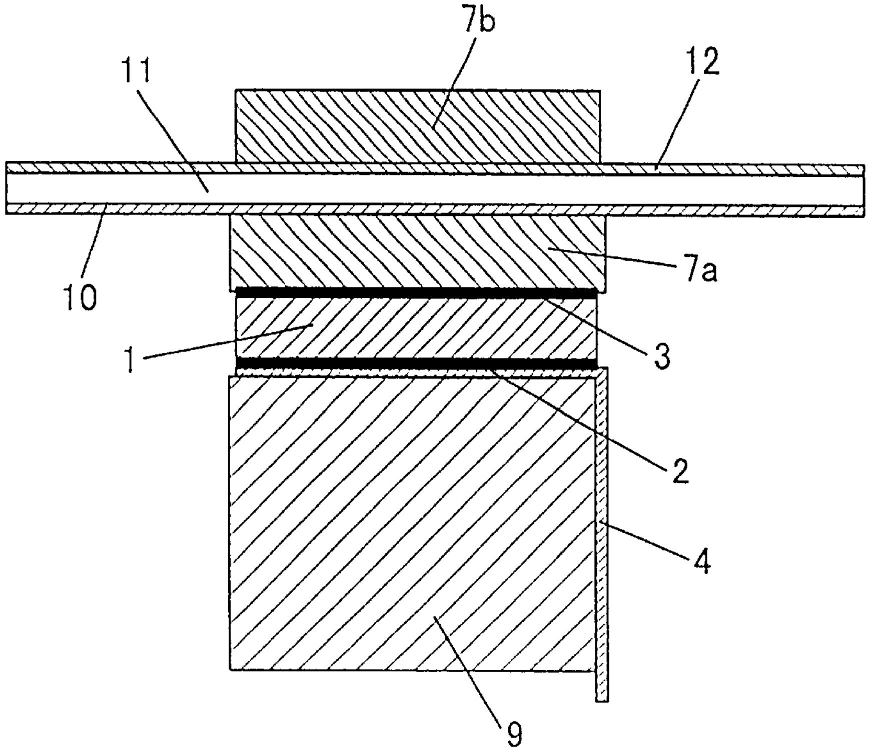
FIG. 3 is a schematic cross sectional view of an ultrasonic probe of a third embodiment according to the present invention.

FIG. 3 is a schematic cross sectional view of an ultrasonic probe of a third embodiment according to the present invention.

The third embodiment of the present invention provides an ultrasonic probe which allows an electrical terminal to be easily extended from an electrode of the piezoelectric element, and also allows good sensitivity and frequency characteristics in transmitting and receiving the ultrasonic wave to be secured because the high molecular material also serves as a part of the acoustic matching layer. The third embodiment further makes it possible to reduce noise since a shield effect is enhanced by a conductive layer formed on a face of the high molecular material layer located on an acoustic matching layer side.

Referring to FIG. 3, reference numerals 1 to 11 are similar to those of the first and second embodiments shown in FIGS. 1 and 2. That is, the ultrasonic probe of the third embodiment of the present invention has a piezoelectric element 1, a ground electrode 3, a positive electrode 2, a signal electrical terminal 4, a backing material 9, a high molecular material layer 11, a conductive layer 10, a first acoustic matching layer 7*a* located on the piezoelectric element side, and a second acoustic matching layer 7*b* provided on the high molecular material layer 11.

The functions of these components will not be described herein since they have already been described with reference to the first and second embodiments. In the third embodiment, a conductive layer 12 for shielding is provided between the high molecular material layer 11 and the second acoustic matching layer 7*b*.

The conductive layer 12 is directly formed on the high molecular material layer 11 by deposition, sputtering, or plating with copper, nickel, silver, gold or the like. The conductive layer 12 may be formed on the second acoustic matching layer side by the same method. Preferably, this conductive layer 12 is not electrically connected to the conductive layer 10 which is electrically connected to the ground electrode 3, but is electrically connected to a shield line of a cable which connects the ultrasonic probe to the main body. Further, since a thin conductive layer 12 with a thickness of only a few $\mu$m is enough to provide the shield effect, this layer hardly affects the sensitivity and frequency characteristics in transmitting and receiving the ultrasonic wave. The conductive layer 12 with such a thickness causes no problem at all.

Though, in the embodiments of the present invention described above, two acoustic matching layers are employed, a similar effect can be obtained in other cases where one or three or more acoustic matching layers are employed.

Employing an ultrasonic probe configured as described above allows an image obtained from an ultrasonic diagnostic apparatus to be of higher resolution and of higher sensitivity, and further, provides an ultrasonic probe capable of reducing noise, since the conductive layer 12 works as a shield.

Figure 4:
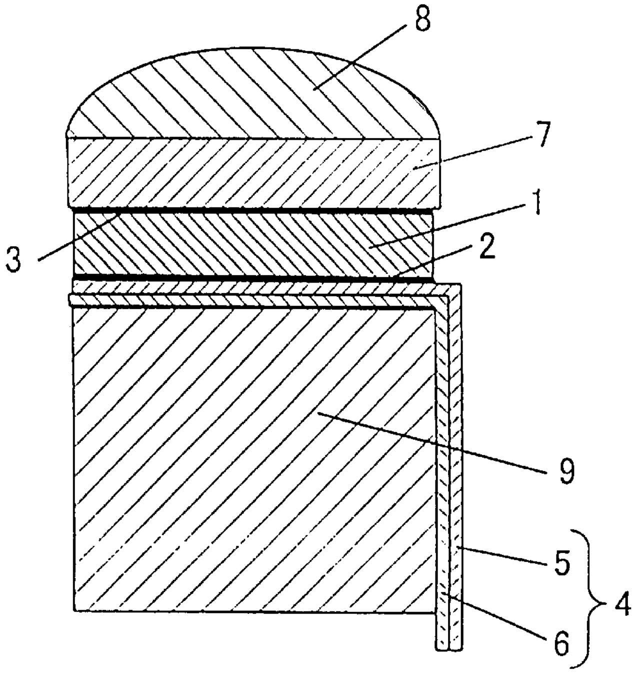
FIG. 4 is a schematic cross sectional view of an ultrasonic probe of a fourth embodiment according to the present invention.

FIG. 4 is a schematic cross sectional view of an ultrasonic probe of a fourth embodiment of the present invention. A piezoelectric element 1 is made ofa piezoelectric ceramic including PZT-based material, single crystal, or high molecular material such as PVDF (poly-vinylidene fluoride) to be used for transmitting and receiving an ultrasonic wave. Each of electrodes 2, 3 is provided on each face of the piezoelectric element 1, respectively. These electrodes 2,3 are formed by sputtering, deposition, or baking with a metal such as gold, silver or the like. An acoustic matching layer 7 is provided on electrode 3. This acoustic matching layer is composed of one or more layers mainly made of resin or graphite for achieving an acoustic matching between the piezoelectric element 1 and a subject to be examined (human body, not shown). An acoustic lens 8 is provided on the acoustic matching layer 7 . This acoustic lens is mainly made of silicone rubber for converging, diverging and deflecting the ultrasonic wave.

A signal electrical terminal 4 is provided on electrode 2. The signal electrical terminal 4 comprises a conductive layer 5 contacting the electrode 2, and an insulator 6 located on the other side of the conductive layer 5 with respect to the electrode 2. The conductive layer 5 is formed by laminating a conductive material such as metal or the like on the insulator 6 using a method such as sputtering, deposition, baking or the like. The conductive layer 5 is electrically connected to the piezoelectric element 1. A backing material 9 is provided on the insulator 6 of the signal electrical terminal 4. The backing material 9 is made of epoxy resin of ferrite-mixed rubber, and is bonded to the insulator 6 so as to provide a damping effect to the piezoelectric element 1 and also to mechanically support it.

The signal electrical terminal 4 is laterally extended out from a connecting portion of the piezoelectric element 1 and the backing material 9, and then is folded along a side face of the backing material 9.

In order to electrically connect the piezoelectric element 1 to the conductive layer 5, they are bonded to each other by performing a bonding method using a conductive adhesive or by the so-called ohmic contact method using a very thin bonding layer of epoxy resin.

In order to avoid adversarial affects on the damping effect of the backing material 9, the signal electrical terminal 4 must be thin enough. The conventional conductive layer 5 employed in an ultrasonic probe with, for example, a setting frequency of 3.5 MHz has a thickness less than 1/400 wavelength, and accordingly, has substantially no adversarial affect on the acoustic characteristic of the ultrasonic probe. However, when the insulator 6 of the signal electrical terminal 4 is thick, it affects the acoustic characteristic. Accordingly, the thickness of the insulator 6 must be thin enough so as not to affect the acoustic characteristic.

Figure 5:
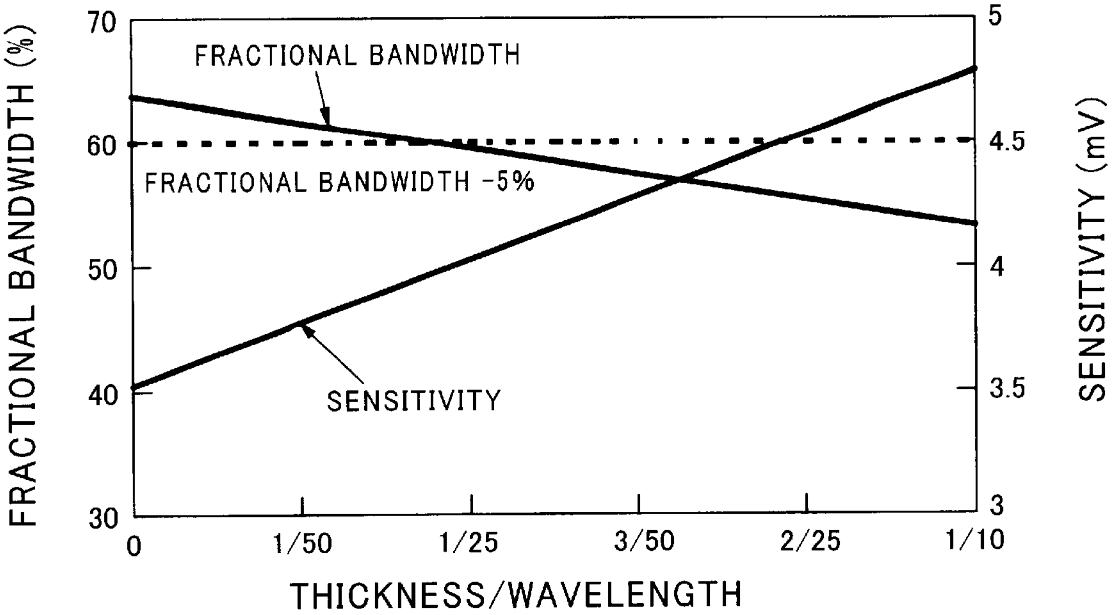
FIG. 5 shows a calculation result of an acoustic characteristic when the thickness of polyimide as an insulator is varied.

As a first example of the fourth embodiment, an ultrasonic probe structured as shown in FIG. 4 was made using PZT-based piezoelectric ceramic for the piezoelectric element 1, ferrite-mixed rubber having an acoustic impedance of 7 MRayl for the backing material 9, and polyimide (acoustic velocity=about 2250 m/sec, acoustic impedance=about 3 MRayl) for the insulator 6. FIG. 5 shows a calculation result of an acoustic characteristic when the thickness of the insulator 6 is varied in the first example with a setting frequency of the ultrasonic wave being set to 3.5 MHz. The horizontal axis designates a numerical value calculated by dividing the thickness of the insulator 6 by the ultrasonic wavelength. The first vertical axis designates a fractional bandwidth (fractional bandwidth=bandwidth÷center frequency) of −6 dB level, in which a larger fractional bandwidth value means a higher resolution of the ultrasonic probe. The second vertical axis designates a sensitivity value in which a larger sensitivity value mean a higher sensitivity of the ultrasonic probe. The dotted line designates a level where the fractional bandwidth is reduced by 5% from the case where the thickness of the insulator 6 is 0 mm. FIG. 5 clearly shows that as the thickness of the insulator 6 increases, the sensitivity is improved while the fractional bandwidth is reduced.

It is desirable that there is little degradation of the characteristic of the ultrasonic probe, but the characteristic is inevitably varied during an actual manufacturing process. The degradation in the resolution causes no problem if the difference is not observable in the ultrasonic image. This unobservable level causing no problem results at about −7.5% degradation in the characteristic of fractional bandwidth, and this value shall be accomplished for an entire ultrasonic probe, including the variances in respective materials and respective bonded layers. Accordingly, the degradation in the fractional bandwidth caused by the thickness of the insulator 6 shall be reduced further. The thickness of the insulator 6 shall be thin enough so that the degradation in the fractional bandwidth is less than −5% as compared with the case where the thickness of the insulator 6 is 0 mm. FIG. 5 shows that the thickness of the insulator shall be less than 1/25 wavelength of the ultrasonic wavelength in order to make the fractional bandwidth degradation smaller than −5% as compared with the case where the thickness of the insulator 6 is 0 mm.

Figure 6:
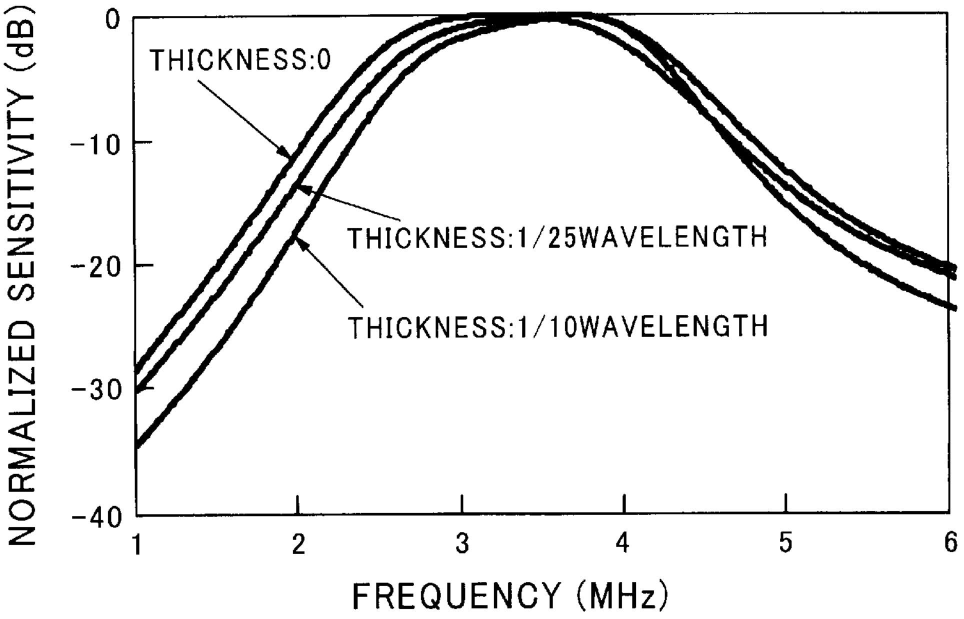
FIG. 6 shows a frequency characteristic when the thickness of polyimide as the insulator is varied.

FIG. 6 is a graph illustrating a calculation result of a frequency characteristic when the central frequency of the ultrasonic probe using the insulator 6 of the first example is set to 3.5 MHz. FIG. 6 shows the normalized sensitivity for transmitting and receiving the ultrasonic wave as a function of the driving frequency. FIG. 6 shows three cases where the thickness of the insulator 6 is 0 mm, equal to or smaller than 1/25 wavelength (1/25 wavelength), or larger than 1/25 wavelength (1/10 wavelength). FIG. 6 shows that the fractional bandwidth is about 62% when the thickness of the insulator 6 is 0 mm, is about 61% when this thickness is equal to or less than 1/25 wavelength (1/25 wavelength), and is about 53% when this thickness is larger than 1/25 wavelength (1/10 wavelength). As can be seen from FIG. 6, the fractional bandwidth of the ultrasonic probe is reduced when an insulator 6 having a thickness equal to or more than 1/25 wavelength is employed.

Thus, by controlling the thickness of the insulator 6 to be equal to or smaller than 1/25 wavelength, the sensitivity of an ultrasonic for transmitting and receiving the ultrasonic wave can be improved and also a good frequency characteristic can be obtained.

Though polyimide was employed as a material for the insulator 6 in the first example, other materials such as polyethylene-terephthalate, poly-sulphon, polycarbonate, polyester, polystyrene, or poly-phenylene-sulphide can also be employed.

Figure 7:
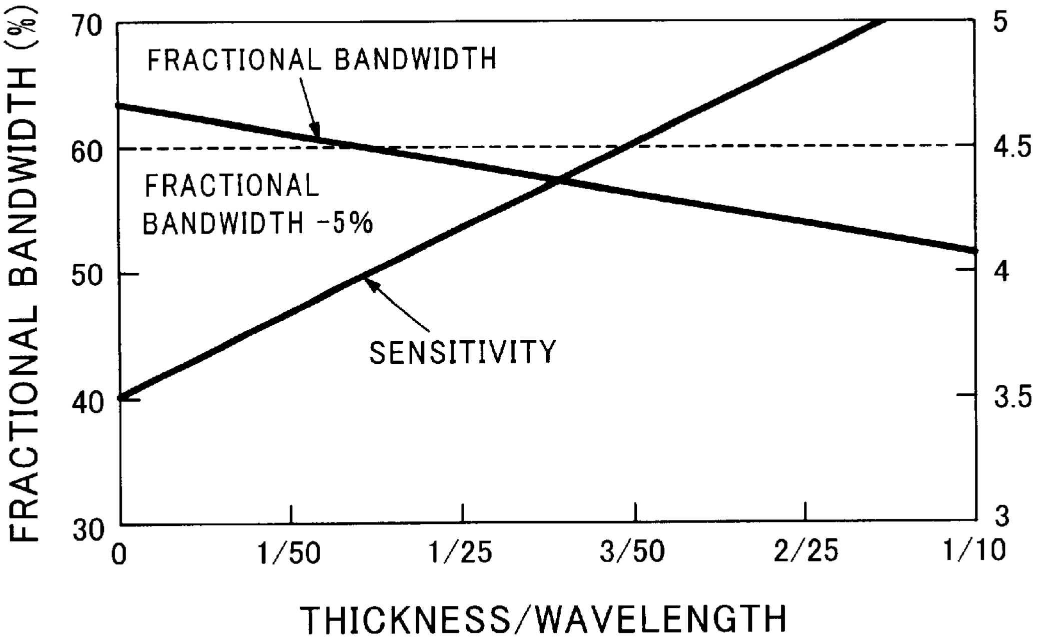
FIG. 7 shows a calculation result of an acoustic characteristic when the thickness of polyethylene-terephthalate as the insulator is varied.

As a second example, an ultrasonic probe structured as shown in FIG. 4 was manufactured using polyethylene-terephthalate as the insulator 6. The piezoelectric element 1 and the backing material 9 are similar to those of the first example. FIG. 7 shows a calculation result of an acoustic characteristic when the thickness of the insulator 6 is varied in the second example with a setting frequency of 3.5 MHz.

Figure 8:
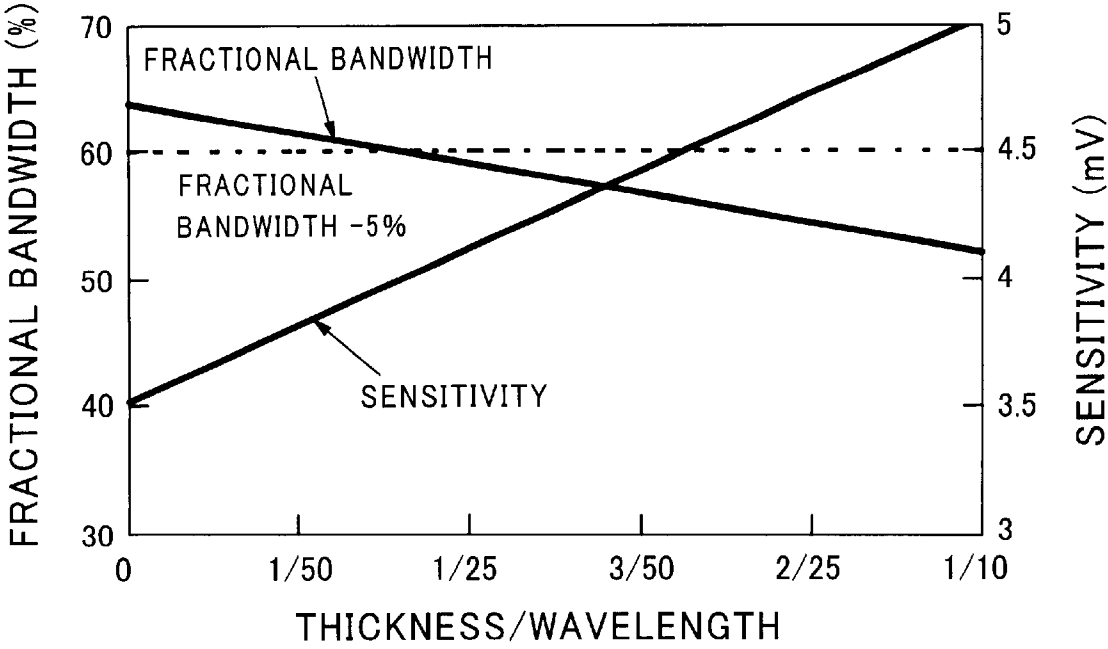
FIG. 8 shows a calculation result of an acoustic characteristic when the thickness of poly-sulphon as the insulator is varied.

As a third example, an ultrasonic probe structured as shown in FIG. 4 was manufactured using poly-sulphon as the insulator 6. FIG. 8 shows a calculation result of an acoustic characteristic when the thickness of the insulator 6 is varied in the third example with a setting frequency of 3.5 MHz.

In both FIGS. 7 and 8, as the thickness of the insulator 6 increases, the fractional bandwidth is reduced while the sensitivity is improved. Both FIGS. 7 and 8 show that the thickness of the insulator 6 shall be equal to or smaller than 1/25 wavelength in order to keep the reduction of the fractional bandwidth equal to or smaller than 5% as compared with the case where the thickness of the insulator 6 is 0 mm.

Thus, even if such material as polyethylene-terephthalate or poly-sulphon is employed as an insulator 6, by making the thickness of the insulator equal to or smaller than 1/25 wavelength, as in the case of polyimide employed as an insulator 6, the sensitivity of an ultrasonic probe in transmitting and receiving the ultrasonic wave can be improved while maintaining a good resolution and a good frequency characteristic.

The acoustic impedance of the material such as polyimide, polyethylene-terephthalate, poly-sulphon, polycarbonate, polyester, polystyrene, or poly-phenylene-sulphide is within the range of 2 to 4 MRayl. Generally speaking, since the material of the piezoelectric element 1 is selected to have the acoustic impedance of about 30 MRayl, and that of the backing material 9 is selected to have the acoustic impedance of about 5 to 10 Mrayl, it is preferable that the thickness of the insulator 6 be adjusted to be equal to or smaller than 1/25 wavelength, and also that the acoustic impedance of the insulator 6 be less than the acoustic impedances of the piezoelectric element 1 and the backing material 9.

Figure 9:
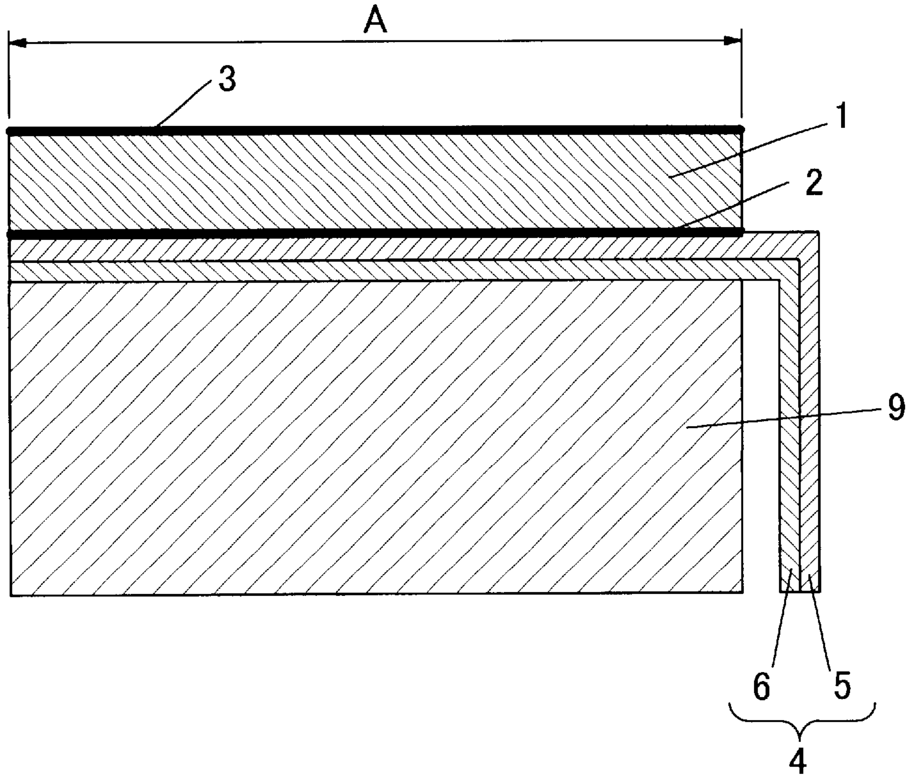
FIG. 9 is an enlarged partial cross sectional view of a piezoelectric element, a backing and a signal electric terminal of the ultrasonic probe of the fourth embodiment according to the present invention.

FIG. 9 is a partial enlarged cross sectional view of the ultrasonic probe of the fourth embodiment of the present invention shown in FIG. 4, illustrating a piezoelectric element, a backing 9 and a signal electric terminal 4 thereof. In FIG. 9, the insulator 6 of the signal electrical terminal 4 shall have a thickness equal to or smaller than 1/25 of the ultrasonic wavelength in the portion (portion A) facing an ultrasonic wave emitting surface of the piezoelectric element 1. However, at the portion of the signal electrical terminal 4 laterally extending from the connecting portion of the piezoelectric element 1 and the backing material 9, the thickness of the insulator need not be controlled because the extended portion does not affect the acoustic impedance of the ultrasonic probe.

Further, in the case of an electronic scanning type ultrasonic probe, the piezoelectric element 1, the signal electrical terminal 4, and a part of the backing material 9 are divided by machining or the like in order to be formed into a plurality of elements aligned along a scanning direction. Accordingly, it is not necessary to apply patterning to the portion A of the conductive layer 5. Further, if the signal electrical terminal 4 is attached to an ultrasonic wave emitting surface of the piezoelectric element 1 covering as wide an area thereof as possible, the electrical connection is impaired little even if the piezoelectric element 1 is cracked by an external mechanical impact, and thereby the ultrasonic probe is less likely to fail and the electrical signal can be transmitted and received well.

As described above, the ultrasonic probe structured according to the fourth embodiment can achieve a highly sensitive acoustic characteristic without degrading the frequency characteristic thereof. Further, the high quality ultrasonic probe can be provided since the structure thereof causes no electrical problem by a possible breakage of wire even if the piezoelectric element is cracked by a mechanical impact or the like.

Figure 10:
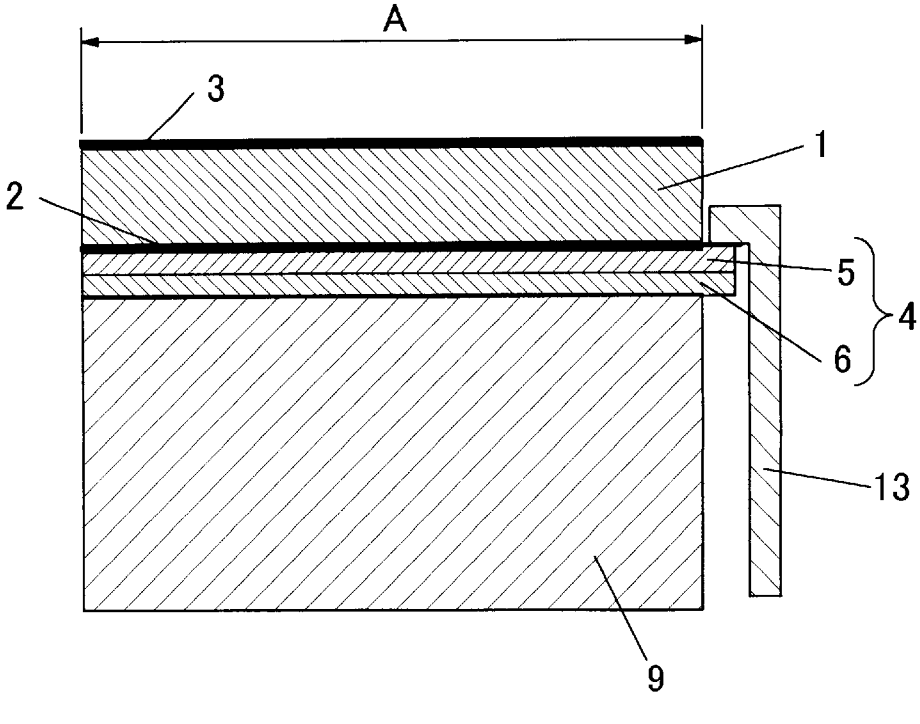
FIG. 10 is an enlarged cross sectional view of an ultrasonic probe of a fifth embodiment according to the present invention.

FIG. 10 is an enlarged cross sectional view of an ultrasonic probe of a fifth embodiment according to the present invention, which corresponds to FIG. 9 of the fourth embodiment. In the fifth embodiment, a signal electrical terminal is divided into a first signal electrical terminal 4 disposed between a piezoelectric element 1 and a backing material 9, and a second signal electrical terminal 13 disposed outside a connecting portion of the piezoelectric element 1 and the backing material 9. In the fifth embodiment, the piezoelectric element 1 and the backing material 9 are similar to those of the fourth embodiment. The first signal electrical terminal 4 is provided on the electrode 2. The first signal electrical terminal 4 comprises a conductive layer 5 contacting the electrode 2, and an insulator 6. The conductive layer 5 is formed on the insulator 6 by attaching thereon conductive material such as metal using such a method as sputtering, deposition, baking or the like. The conductive layer 5 is electrically connected to the piezoelectric element 1. The insulator 6 is bonded to the backing material 9.

The second signal electrical terminal 13 is disposed outside the connecting portion of the piezoelectric element 1 and the backing material 9. The second signal electrical terminal 13 is formed by attaching a patterned conductive material onto an insulator using such a method as sputtering, deposition, baking or the like.

In order to electrically connect the piezoelectric element 1 to the conductive layer 5, they are bonded to each other by performing a bonding method using a conductive adhesive or by the so-called ohmic contact method using a very thin bonding layer of epoxy resin.

In order to connect the conductive layer 5 to the conductive layer to a conductive layer of the second signal electrical terminal 13 at a location outside of the ultrasonic wave emitting surface (portion A), they are bonded to each other by performing a bonding method using a conductive adhesive or by the so-called ohmic contact method using a very thin bonding layer of epoxy resin.

In the fifth embodiment of the present invention, the sensitivity of the ultrasonic probe for transmitting and receiving the ultrasonic wave can be improved and simultaneously a good frequency characteristic can be obtained by, as in the fourth embodiment, adjusting the thickness of the insulator 6 of the first signal electrical terminal 4 to be equal or smaller than 1/25 wavelength. Further, the thickness of the insulator 6 need not be controlled in the area other than that covering the ultrasonic wave emitting surface (portion A) since the acoustic impedance of the ultrasonic probe is not affected thereby.

Also in the fifth embodiment, a preferable material employable as the insulator 6 is polyimide, polyethylene-terephthalate, poly-sulphon, polycarbonate, polyester, polystyrene, poly-phenylene-sulphide or the like. The acoustic impedance of polyimide, polyethylene-terephthalate, poly-sulphon, polycarbonate, polyester, polystyrene, poly-phenylene-sulphide or the like is within the range of 2 to 4 MRayl. Generally speaking, since the material of the piezoelectric element 1 is selected to have an acoustic impedance of about 30 MRayl, and that of the backing material 9 is selected to have an acoustic impedance of about 5 to 10 Mrayl, it is preferable that the thickness of the insulator 6 is adjusted to be equal to or smaller than 1/25 wavelength, and also that the acoustic impedance of the insulator 6 is smaller than the acoustic impedance of the piezoelectric element 1 and the backing material 9.

Further, also in the fifth embodiment, in the case of an electric scanning type ultrasonic probe, in order for it to be formed into a plurality of elements aligned along the scanning direction, the piezoelectric element 1, the signal electrical terminal 4, and a part of the backing material 9 are divided by machining or the like. Accordingly, it is not necessary to apply patterning to the portion A of the conductive layer 5. Further, if the signal electrical terminal 4 is attached to an ultrasonic wave emitting surface of the piezoelectric element 1 covering as wide an area thereof as possible, the electrical connection is impaired little even if the piezoelectric element 1 is cracked by an external mechanical impact, and thereby the ultrasonic probe is less likely to fail and the electrical signal can be transmitted and received well.

As described above, the ultrasonic probe of the fifth embodiment also can achieve a highly sensitive acoustic characteristic without degrading the frequency characteristic thereof, as in the case of the ultrasonic probe of the fourth embodiment. Further, the high quality ultrasonic probe can be provided since the structure thereof causes no electrical problem by a possible breakage of wire even if the piezoelectric element is cracked by a mechanical impact or the like.

Further, in the ultrasonic probe of the fifth embodiment, since the signal electrical terminal is divided into a first signal electrical terminal (the thickness of which must be precisely controlled) and a second signal electrical terminal (the thickness of which need not be precisely controlled), the first and the second signal electrical terminals having different thickness from each other can be manufactured separately and are not required to be folded. Accordingly, the ultrasonic probe of the fifth embodiment is advantageous over that of the first embodiment, with regard to manufacturing.

Figure 11:
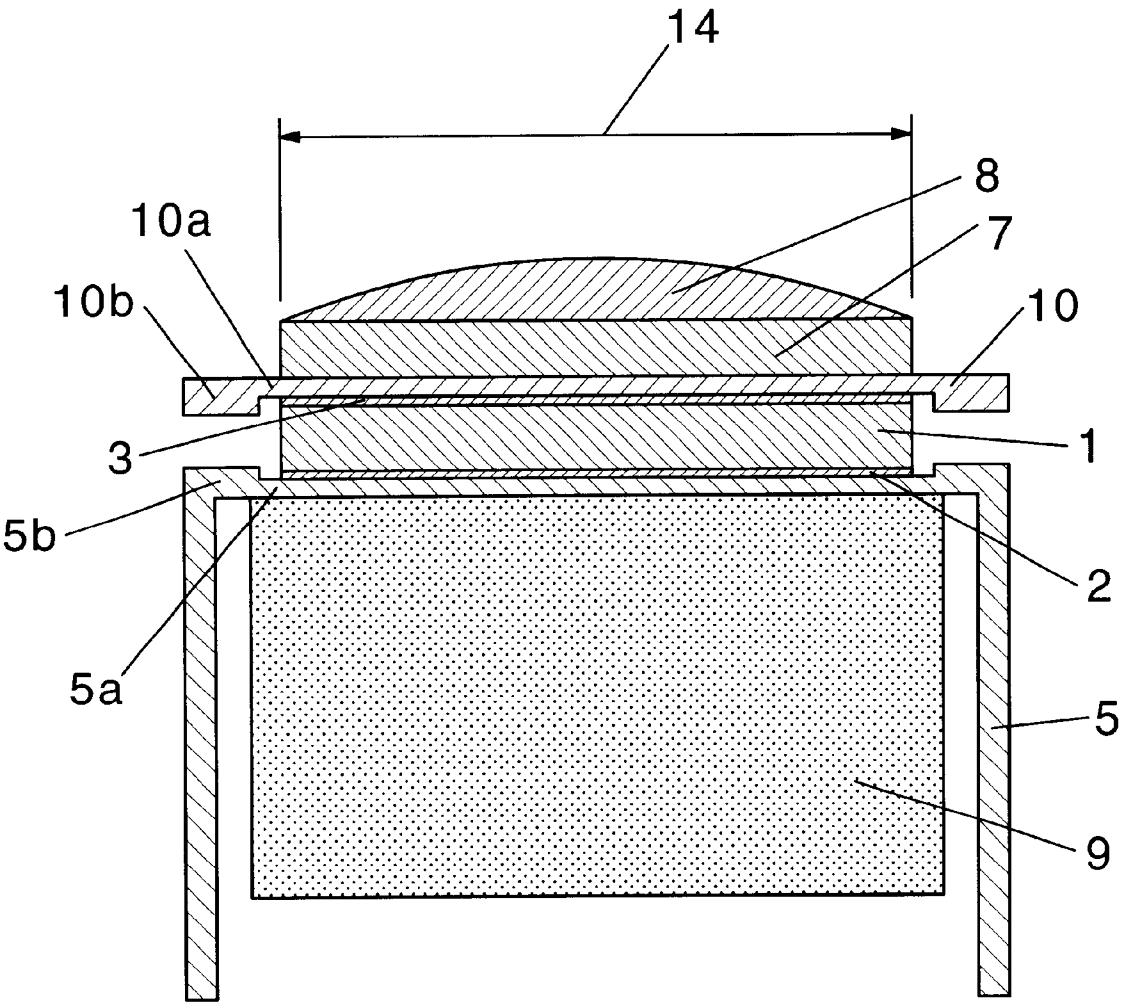
FIG. 11 shows an ultrasonic probe of a sixth embodiment according to the present invention.

FIG. 11 shows an ultrasonic probe of a sixth embodiment according to the present invention.

FIG. 11, the piezoelectric element 1 is an electrostrictive element made of piezoelectric ceramic or the like, and the thickness thereof is optimized based on a driving frequency. The piezoelectric element 1 is provided, in advance, with a ground electrode 3 on a front face thereof and with a positive electrode 2 on a back face thereof. These electrodes have a thickness of 0.5 to 10 $\mu$m and are formed by performing such methods as sputtering, deposition or plating with gold, though the material is not limited to gold. The piezoelectric element 1 sandwiched between the positive electrode 2 and the ground electrode 3 has an acoustically effective area 14 which is subjected to a polarizing action, and thereby substantially transmits and receives an ultrasonic wave. A ground electrode side conductive layer 10 is provided on a front face of the ground electrode 3 to be electrically connected thereto, and this ground electrode side conductive layer 10 is made of conductive material having a different thickness depending on areas thereof, such that a ground electrode side conductive layer portion **10*a*** (thin portion)

covering at least the acoustically effective area 14 has a thickness of 0.5 to 10 μm while another portion (thick portion) 10*b* has a thickness of 15 to 50 μm.

The ground electrode side conductive layer 10 having the different thickness depending on the areas thereof can be formed by a method comprising the steps of applying a mask of a desired pattern to a copper foil having a thickness of 0.5 to 10 μm, plating a conductive layer on the foil through the mask, and then removing the mask. The ground electrode side conductive layer 10 can also be formed by an alternative method comprising the steps of applying a desired mask to a copper foil having a thickness of 15 to 50 μm, performing an etching process through the mask to make the copper partially thinner, and then removing the mask. Further, the ground electrode side conductive layer 10 is provided, on a front face of thereof, with an acoustic matching layer 7 for obtaining an acoustic matching and an acoustic lens 8 made of such material as silicone rubber for focusing the ultrasonic wave.

On the other hand, a positive electrode side conductive layer 5 made of such electrically conductive material as copper foil is laminated onto a back face of the positive electrode 2 so as to be electrically connected to the positive electrode 2. This positive electrode side conductive layer 5 is, same as the ground electrode side conductive layer 10, made of conductive material having a different thickness depending on areas thereof, such that a positive electrode side conductive layer portion 5*a* (thin portion) covering at least the acoustically effective area 14 has a thickness of 0.5 to 10 μm while another portion (thick portion) 5*b* has a thickness of 15 to 50 μm. The positive electrode side conductive layer 5 can be formed by a similar method employed for the ground electrode side conductive layer 10, and can be provided with a desired pattern in advance, if necessary. A backing material 9 is provided on a back face of the positive electrode side conductive layer 5 to complete the ultrasonic probe.

Though, in the structure described above, the thickness of both conductive layers on the positive electrode side on the ground electrode side is partially varied, the thickness may be partially varied in only one of the positive and the ground electrode side conductive layers. This can also be applied to the case where the conductive layer on either side is partially extended over the acoustically effective area. Further, though copper is employed as the conductive material in the above description, such conductive materials as silver, nickel, etc. may be employed without being limited to copper. Further, though, in the description above, there is only one acoustic matching layer, there may be employed two or more acoustic matching layers.

According to the above structure, there is provided an advantageous effect in that, since the conductive layer has different thicknesses such that the area covering the electrode portion of the piezoelectric element is thinner than other areas thereof, acoustic mismatch can be suppressed because of the thin conductive layer within the acoustically effective area 14, where an ultrasonic vibration is actually generated and the acoustic matching is required. At the same time, the electrical signal can be transmitted at a low electrical impedance because of the thick portion at the other areas of the conductive layer used as electrically conductive path portions.

According to the embodiments of the present invention, as in obvious from the description above, even if a material causing a mismatch in terms of acoustic impedance exists within the acoustically effective area 14, the negative effect due to the acoustic mismatch can be limited to an extremely low level when the thickness thereof is equal to or smaller than 1/20 wavelength of the ultrasonic wave to be transmitted and received. Thereby, an ultrasonic probe of high sensitivity and high resolution can be provided without degradin the frequency characteristic in transmitting and receiving the ultrasonic wave, and without degrading the sensitivity, by making the thickness of the conductive layer equal to or smaller than 5 μm within the acoustically effective area 14; though it depends on the designed frequency of the ultrasonic probe.

Further, since the electrical impedance can be controlled to be low by making the conductive layer serving as the electrically conductive path thick, a capacity for removing external electrical noise can be improved, and thereby an ultrasonic diagnostic image of high sensitivity and high resolution can be provided without any deterioration of the diagnostic image due to external electromagnetic wave noise.

According to the present invention, the structure described above can simultaneously optimize both an acoustic matching condition and electrical conductive path, and can provide information based on an ultrasonic diagnostic image of high accuracy.

Figure 12:
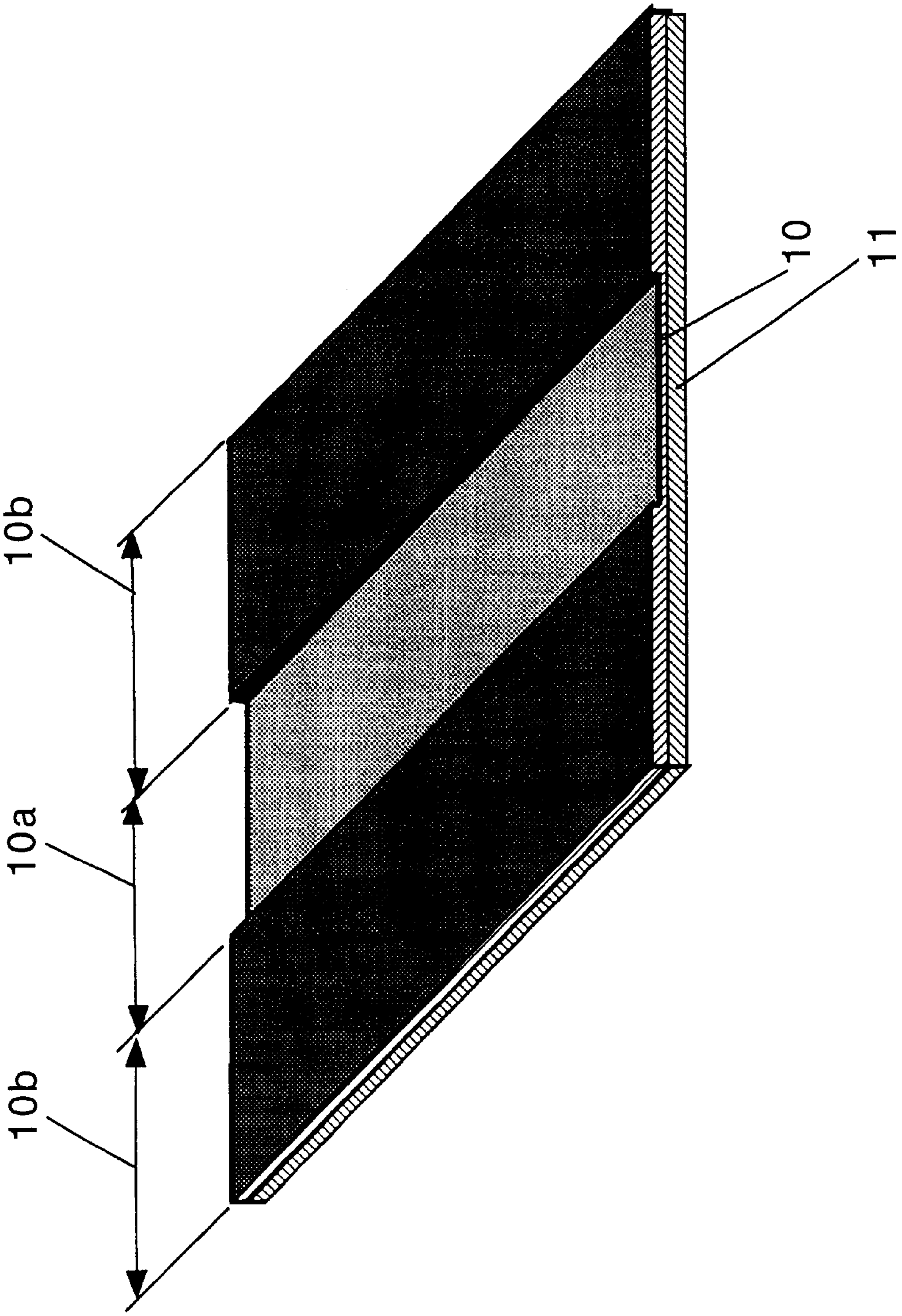
FIG. 12 is a perspective view illustrating a structure of a base material layer and a conductive layer formed beforehand on the base material layer, wherein the thickness of the conductive layer varies depending on an area thereof.

FIG. 12 is a perspective view, illustrating a structure of a conductive layer formed beforehand on a base material layer in place of the conductive layer of the sixth embodiment, wherein the thickness of the conductive layer is partially different from other parts therein.

In FIG. 12, a ground electrode side base material layer 11 is made of, for example, insulating high molecular film of polyimide with a thickness of about 5 to 50 μm, and a ground electrode side conductive layer 10 having different thickness depending on areas thereof is formed on one surface of the base material layer 11. This ground electrode side conductive layer 10 has, in a middle part thereof, a ground electrode side conductive layer 10*a* (thin portion) covering at least the acoustic effective area 14, and other ground electrode side conductive layers 10*b* (thick portion) disposed on both sides of the thin portion, wherein the thickness of the thin portion is preferably 0.5 to 10 μm and that of the thick portion is preferably 15 to 50 μm.

This ground electrode side conductive layer 10 having the different thickness depending on the areas thereof can be formed by a method comprising the steps of forming a copper layer with a thickness of 0.5 to 10 μm of a base material layer made of polyimide with a thickness of 5 to 50 μm by plating, sputtering, or the like, applying a mask of a desired portion an area of the copper layer to be kept thin, plating areas of the copper layer to be made thick with conductive material, and then removing the mask.

The ground electrode side conductive layer 10 can also be formed by an alternative method comprising the steps of plating a base material of polyimide with copper 15 to 50 μm thick, applying a mask of a desired pattern to a portion of the copper to be kept thick, partially etching a non-masked portion of the copper to make it thinner, and then removing the mask.

The manufacturing processes of the ground electrode side conductive layers described above are similar to those generally employed in the production of a flexible print circuit.

FIG. 12 shows a structure of the ground electrode side conductive layer having the different thickness depending on the areas of the conductive layer, and an electrode side conductive layer has the same structure. At that time, a desired pattern can be applied to the electrode side conductive layer, if necessary.

Further, the material of the base material layer is not limited to polyimide, but other materials that are hard to be plastically deformed may be employed.

As described above, employing the conductive layer formed on the base material layer provides such a remarkable advantageous effect in that, in addition to the operation and effect of the sixth embodiment, the conductive portion formed by the thinner portion of the conductive layer is not likely to be creased, crinkled or eventually plastically deformed, which makes it easy to handle the conductive layer and the ultrasonic probe during the production processes thereof.

Figure 13:
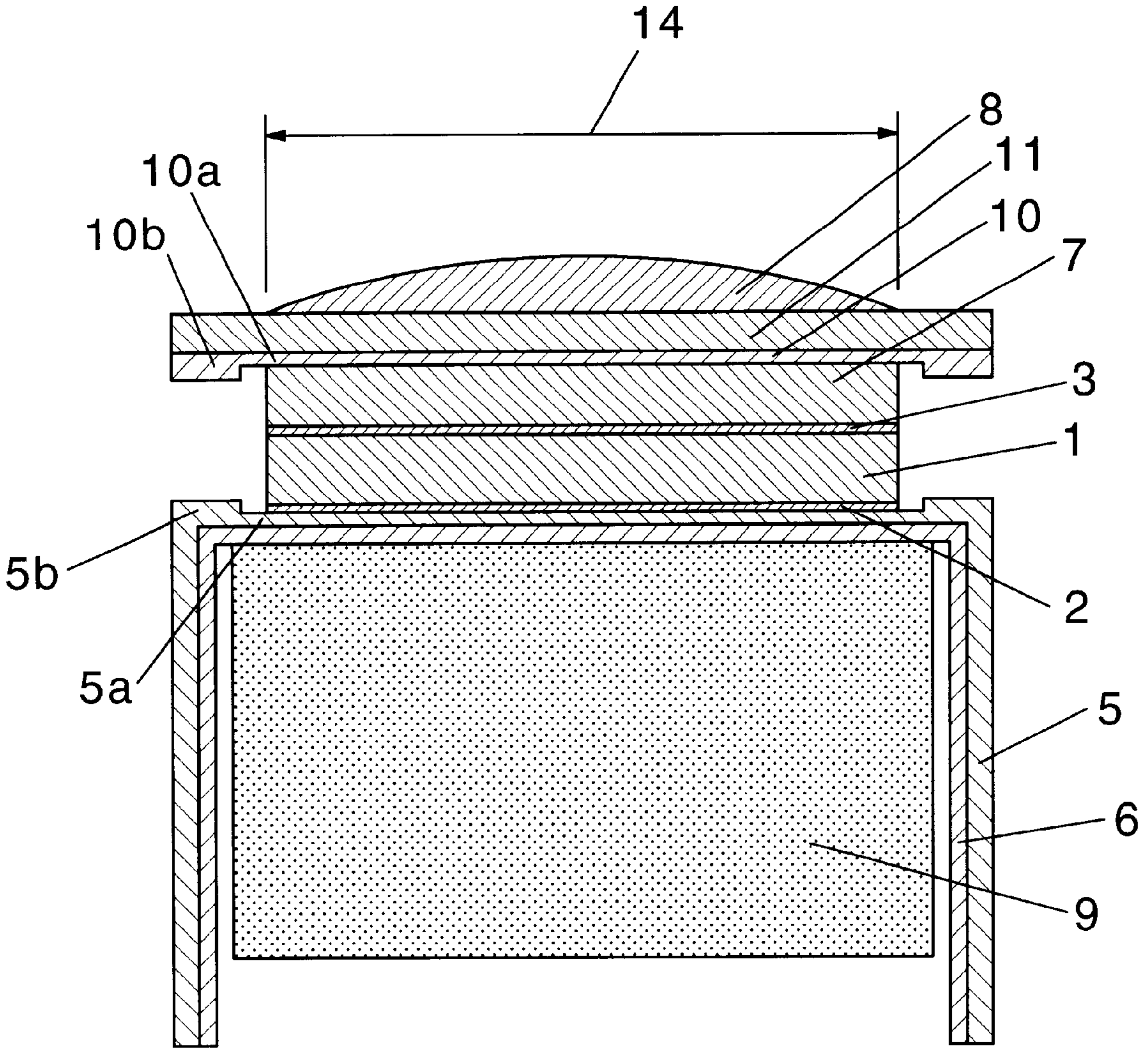
FIG. 13 shows an ultrasonic probe of a seventh embodiment according to the present invention.

FIG. 13 shows an ultrasonic probe of a seventh embodiment according to the present invention.

Referring to FIG. 13, the ultrasonic probe of the seventh embodiment comprises a piezoelectric element 1 having a positive electrode 2 on one face thereof and having a ground electrode 3 on the other face thereof, an acoustic matching layer 7 provided on a front face of the ground electrode 3; a ground electrode side conductive layer 10 provided on a front face of the acoustic matching layer 7 and on a ground electrode side base material layer 11, with the conductive layer 10 having a different thickness depending on areas thereof; and an acoustic lens 8 provided on a front face of the ground electrode side base material layer 11. According to the structure described above, the present invention provides an ultrasonic probe in which the ground electrode side base material layer 11 works as a second acoustic matching layer.

In FIG. 13, the acoustic matching layer 7 is made of electrically conductive material such as graphite so as to be electrically connected to the ground electrode 3 provided on the front face of the piezoelectric element 1. Further, as described in FIG. 12, the ground electrode side base material layer 11 and the ground electrode side conductive layer 10 having different thickness depending on the areas thereof are provided between the acoustic matching layer 7 and the acoustic lens 8. This ground electrode side conductive layer 10 is formed in advance on the ground electrode side base material layer 11 so as to be electrically connected to the acoustic matching layer 7.

In this structure, it is preferable that the ground electrode side base material layer 11 is designed to work as an acoustic matching layer. That is, it is preferable that the acoustic impedance of the material of the ground electrode side base material layer 11 is between those of the acoustic matching layer 7 and the acoustic lens 8, and the thickness thereof is about a quarter wavelength of the ultrasonic wave to be transmitted and received.

If the ground electrode side base material layer 11 is disposed between the ground electrode 3 and the acoustic matching layer 7, it may cause an acoustic mismatch, depending on the acoustic impedance value of the ground electrode side base material layer 11. When the ground electrode side base material layer 11 is disposed between the acoustic matching layer 7 and the acoustic lens 8; however the ground electrode side base material layer 11 can be positively utilized as a second acoustic layer by optimizing the impedance and the thickness thereof. Accordingly, the ultrasonic probe of the seventh embodiment of the present invention not only can avoid the acoustic mismatch but also can optimize the acoustic matching, and thereby an ultrasonic probe of high sensitivity and high resolution can be obtained by improving the sensitivity and the frequency characteristics in transmitting and receiving the ultrasonic wave.

Preferable materials as the ground electrode side base material layer 11 of the seventh embodiment are high molecular films having an acoustic impedance within the range of 2.5 to 4.5 Mrayl such as polyimide, polyester, polycarbonate or polyethylene.

Other operations and effects of the ultrasonic probe of the seventh embodiment are similar to those of the sixth embodiment, and those of the ultrasonic probe employing the base material layer 11 shown in FIG. 12.

Figure 14:
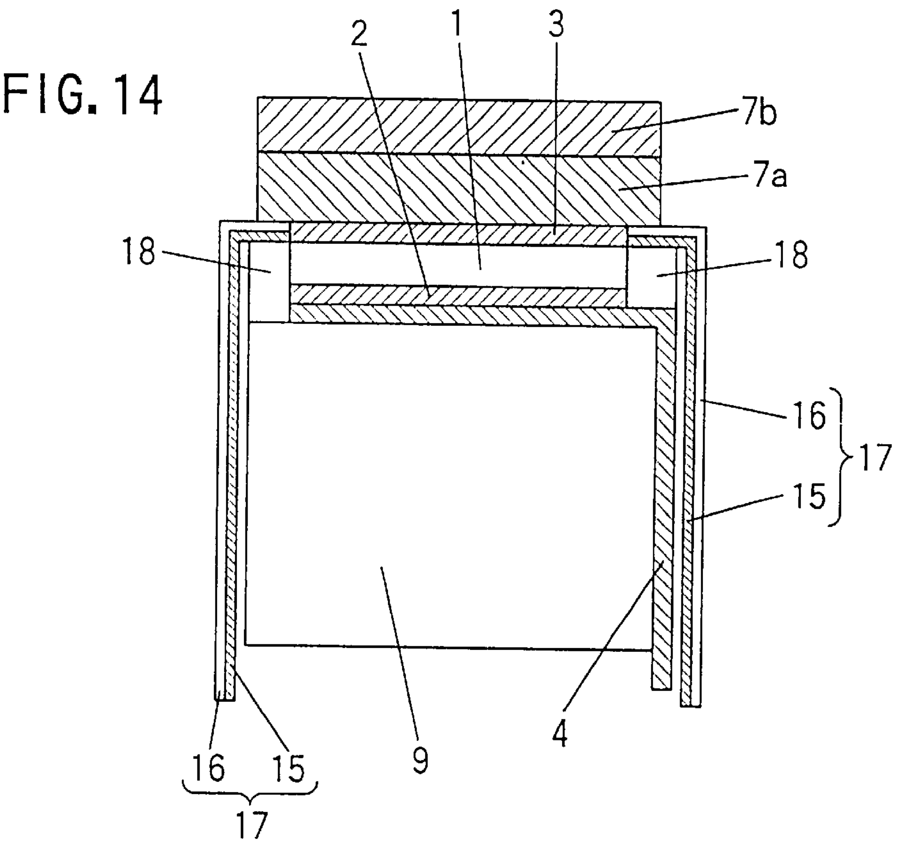
FIG. 14 is a schematic cross sectional view of an ultrasonic probe of an eighth embodiment according to the present invention.

FIG. 14 shows an ultrasonic probe of the eighth embodiment of the present invention. FIG. 14 is a cross sectional view of an ultrasonic probe, taken along a short axis thereof. In explaining this drawing, the word "up" means a direction from the lower part of the drawing to the upper part thereof. (This is also applicable to FIGS. 15 and 16.) In FIG. 14, the piezoelectric element 1 is made of piezoelectric ceramic including PZT-based material, single crystal, or high molecular material such as PVDF. Further, the piezoelectric element 1 is provided with a ground electrode 3 and a positive electrode 2 each disposed on opposite faces thereof, respectively. The ground electrode 3 and the positive electrode 2 are formed by deposition, plating or sputtering using gold, silver, copper, tin, nickel or aluminum, or by baking with silver. A first acoustic matching layer 7*a* is provided on an upper surface of the ground electrode 3 (on the surface facing a subject to be examined) for efficiently transmitting the ultrasonic wave, and is made of conductive material such as graphite.

The first acoustic matching layer 7*a* and the ground electrode 3 are electrically connected to each other by performing a method using a conductive adhesive or by the so-called ohmic contact method using a very thin layer of epoxy resin. A conductive film 17 composed of a base film 15 made of high molecular material and a conductive copper layer 16 is disposed along a side face of a backing material 9 (which will be described later). The conductive film 17 is flexible. The first acoustic matching layer 7*a* is electrically connected at both sides of a lower face thereof to the copper layer 16 of the conductive film 17 by the conductive adhesive. These portions may alternatively be electrically connected with the epoxy layer in accordance with the ohmic contact method as described above. The ground electrode 3 works as a common electrode for GND.

The first acoustic matching layer 7*a* is wider than the piezoelectric element 1, and extends beyond the side of the piezoelectric element 1. A second acoustic matching layer 7*b* is provided on an upper surface of the first acoustic matching layer 7*a* for efficiently propagating the ultrasonic wave, and is made of epoxy resin or high molecular material such as polyimide, polyethylene-terephthalate, polysulphon, polycarbonate, polyester, polystyrene, or polyphenylene-sulphide. Further, an acoustic lens (not shown) made of silicone rubber, urethane rubber or plastics is provided on an upper surface of the second acoustic matching layer 7*b* via an adhesive for focusing the ultrasonic wave.

The positive electrode 2 disposed beneath the piezoelectric element 1 is a signal electrode formed as a pattern on, for example, a high molecular material film, and is electrically connected to FPC 4 by a conductive adhesive. The backing material 9 is made of ferrite-rubber, epoxy or urethane rubber mixed with micro-balloons for holding the piezoelectric element 1 as well as for absorbing undesired ultrasonic waves. At a lateral side of the piezoelectric element 1, an insulating layer 18 is provided in a space formed between an end portion of the acoustic matching layer 7$a$ and that of the backing material 9. The insulating layer 18 is made of insulating material such as epoxy resin, and works to insulate the conductive film 17 from the FPC 4 and the positive electrode 2, as well as to support the end portion of the first acoustic matching layer 7$a$ extending from the piezoelectric element 1.

Though, in this embodiment, a conductive adhesive is used for connecting the conductive film 17 to the first acoustic matching layer 7$a$ and for connecting the positive electrode 2 to the FPC 4, an insulating adhesive may alternatively be used to electrically connect these elements if the adhesive is cured with compression. It is preferable that a layer of gold or nickel is formed on the surface of the copper layer 16 of the conductive film 17 by deposition, plating or sputtering in order to prevent oxidation thereof.

A manufacturing method of the ultrasonic probe having the above structure will now be described according to steps (A) to (I). In step (A), initially, the ground electrode 3 and the positive electrode 2 are formed on the piezoelectric element 1. The piezoelectric element 1 and the FPC 4 are bonded to each other by applying a conductive adhesive onto the positive electrode 2 and the FPC 4, and heating the positive electrode 2 and the FPC 4 while applying pressure thereto to cure the adhesive. In step (B), the first acoustic matching layer 7$a$ and the conductive film 17 are bonded to each other by applying a conductive adhesive to an end of the first acoustic matching layer 7$a$ and the copper layer 16 of the conductive film 17, and heating the acoustic matching layer 7$a$ and the copper layer 16 while applying pressure thereto cure the conductive adhesive. During this process, the conductive film 17 is preferably bonded in its flat condition. In step (C), the backing material 9, the piezoelectric element 1 with the FPC 4 bonded thereto, the first acoustic matching layer 7$a$ with the conductive film 17 bonded thereon, and the second acoustic matching layer 7$b$ are bonded to one another by an adhesive. In step (D), the insulating layer 18 is formed in a space formed between the end portion of the acoustic matching layer 7$a$ and that of the backing material 9. In step (E), the bonded members are cut into arrays with a predetermined pitch by a cutting machine such as a dicer. In step (F), the cut members are bent into a predetermined curvature. In step (G), the cut members are bonded and fixed to a member made of the same material as that of the backing material 9, or of a hard material such as epoxy or metal, or a composite plate made by combining these materials (not shown). In step (H), the FPC4 and the conductive film 17 are bent to form a shape as shown in FIG. 14. In step (I), the acoustic lens (not shown) is bonded onto the second acoustic matching layer 7$b$ by an adhesive.

The above manufacturing method describes how to manufacture a convex type ultrasonic probe, and the same method may be applied to manufacture a linear type ultrasonic probe. In the case of the linear type ultrasonic probe, when the end of the first acoustic matching layer 7$a$ and the copper layer 16 of the conductive film 17 are bonded to each other by applying a conductive adhesive thereto, and heating the copper layer 16 and the acoustic matching layer 7$a$ while applying pressure thereto to cure the conductive adhesive, the conductive film 17 may be bent in advance to form a right angle before bonding occurs. Alternatively, the conductive film 17 may be bent after the adhesive has cured.

Next, an operation of the ultrasonic probe structured as above will be described. A plurality of electrical signals transmitted with arbitrary delays in timing from a transmitting section of a main body of an ultrasonic diagnostic apparatus (not shown) are transmitted through a cable (not shown) and the FPC 4 to a plurality of piezoelectric elements 1 arranged in an array. The piezoelectric element 1 to which the electrical signals are transmitted generates ultrasonic waves, and then the ultrasonic waves propagate through the first acoustic matching layer 7$a$, the second acoustic matching layer 7$b$ and the acoustic lens (not shown). The ultrasonic waves are focused and/or deflected with respect to the scanning direction in response to the timing delay from the transmitting section. The ultrasonic waves are propagated into the patient body. The ultrasonic waves are reflected at the interfaces of the internal organs of the patient by an acoustic impedance difference. The reflected ultrasonic waves are received by the piezoelectric elements 1, converted into electrical signals, and then transmitted through the cable to a receiving section of the main body of the ultrasonic diagnostic apparatus. An internal image of the patient can be visualized on a monitor by processing the signals received by the receiving section and by displaying the image of the received signals on a display section of the main body of the ultrasonic diagnostic apparatus. Though these operations are similar to those of a conventional ultrasonic probe, the application of the ultrasonic probe of the present invention is not limited to the transmitting and receiving method employed in the main body described above.

Preferably, a layer of gold or nickels is formed on the surface of the copper layer 16 of the conductive film 17 by deposition, plating, or sputtering in order to prevent oxidation thereof. Alternatively, the conductive film 17 may be made of a thin layer of copper, aluminum or the like without using a base film 15 of high molecular material. Further, though, in FIG. 14, the positive electrode 2 is extended as FPC 4, how to extend the positive electrode 2 is not limited to this manner. Further, in FIG. 14, the ground electrode 3 is used as a GND electrode and the positive electrode 2 is used as a signal electrode. Further, when a conductive adhesive layer (not shown) is provided on a side of the first acoustic matching layer 7$a$ to strongly fix the conductive film 17 to the first acoustic matching layer 7$a$ and to increase a bonding area therebetween, a contact resistance may be reduced and noise generation may be prevented. Also, the ultrasonic probe can easily manufactured.

As described above, according to the eighth embodiment of the present invention, employing the flexible conductive film 17 facilitates forming of a curved face after a cutting machining operation in case of, for example, the convex type ultrasonic probe. Further, since an electrical connection can be maintained through the conductive first acoustic matching layer even if the piezoelectric element is cracked by a mechanical impact, there can be provided a high quality ultrasonic probe including a convex probe, a linear probe and a matrix probe, in which the performance of the piezoelectric element is not degraded, a fault due to breakage of wire is less likely to occur, and unwanted radiation hardly takes place.

Further, employing the flexible conductive film 17 makes it easy to apply a stable pressure to the bonding face of the first acoustic matching layer, and also provides an advantageous effect in that separation due to handling after bonding is not likely to occur, and thereby an ultrasonic probe can be easily manufactured.

Further, by providing the insulating layer 18 in the space formed on the side of the piezoelectric element 1 and between the first acoustic matching layer 7$a$ and the backing material 9, it possible to support the first acoustic matching layer 7$a$, which strengthens the first acoustic matching layer against a mechanical impact during, for example, a machining process by a dicer, and thereby makes it easy to manufacture the ultrasonic probe.

Further, the electrical connection between the first acoustic matching layer and the conductive film makes it unnecessary to bond to the conductive film to the piezoelectric element using a conductive adhesive of a high curing temperature. As a result, the ultrasonic probe can be easily manufactured without degrading the performance of the piezoelectric element since the piezoelectric element need not be exposed to an environment of high temperature.

Figure 15:
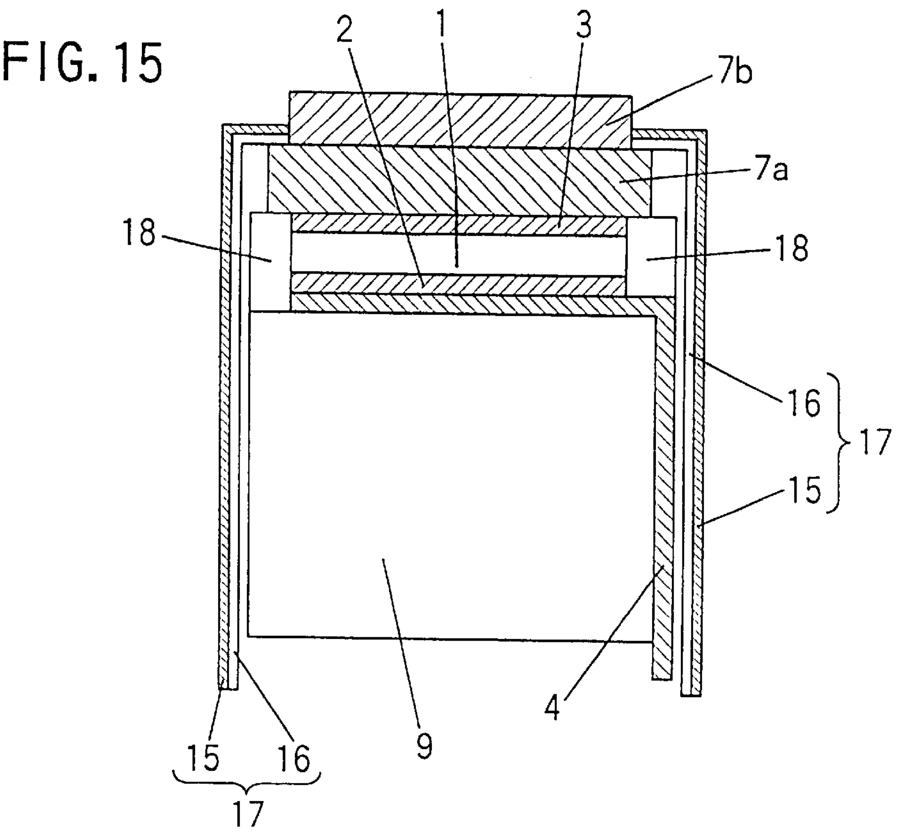
FIG. 15 is a schematic cross sectional view of an ultrasonic probe of a ninth embodiment according to the present invention.

FIG. 15 shows an ultrasonic probe of a ninth embodiment according to the present invention. The ninth embodiment is different from the eighth embodiment in that a copper layer 16 of a conductive film 17 is electrically connected to a first acoustic matching layer *7a* by a conductive adhesive at both side ends of an upper face of the first acoustic matching layer *7a*. As for the components shown in FIG. 15, the piezoelectric element 1, the ground electric 3, the positive electrode 2, the first acoustic matching layer *7a*, the FPC 4, and the backing material 9 are similar to those of the eighth embodiment.

Referring to FIG. 15, the piezoelectric element 1 is provided with the ground electrode 3 and the positive electrode 2 on two opposite faces thereof, respectively. A first acoustic matching layer *7a* is provided on an upper surface of the ground electrode 3 for efficiently propagating an ultrasonic wave. The first acoustic matching layer *7a* and the ground electrode 3 are electrically connected to each other by a method using a conductive adhesive or the so-called ohmic contact method using a very thin layer of epoxy resin.

Further, a flexible conductive film 17 composed of a base film 15 and a conductive copper layer 16 is disposed on each side of the piezoelectric element 1. The copper layer 16 of the conductive film 17 and the first acoustic matching layer *7a* are electrically connected to each other at both side ends of the upper surface of the first acoustic matching layer *7a*. The copper layer 16 and the acoustic matching layer *7a* may also be electrically connected to one another by an insulating resin in accordance with with the ohmic contact method. In this structure, the ground electrode 3 is a common electrode for GND.

The second acoustic matching layer *7b* is provided on the upper surface of the first acoustic matching layer *7a* for efficiently propagating the ultrasonic wave, and is made of high molecular material such as epoxy resin, polyimide, polyethylene-terephthalate, poly-sulphon, polycarbonate, polyester, polystyrene, or poly-phenylene-sulphide. An acoustic lens (not shown) is attached onto an upper surface of the second acoustic matching layer *7b* by an adhesive. This acoustic lens is made of silicone rubber, urethane rubber, or plastic for focusing the ultrasonic wave.

The positive electrode 2 disposed beneath the piezoelectric element is a signal electrode formed as a pattern on, for example, a high molecular material film, and is electrically connected to FPC 4 by a conductive adhesive. The backing material 9 is made of such material as ferrite-rubber, epoxy or urethane rubber mixed with micro-balloons for holding the piezoelectric element 1 and for absorbing undesired ultrasonic waves. At a side of the piezoelectric element 1, an insulating layer 18 is provided in a space formed between an end portion of the first acoustic matching layer *7a* and that the backing material 9. The insulating layer 18 is made of insulating material such as epoxy resin so as to insulate the conductive film 17 from the FPC 4 and the positive electrode 2, and also to support the first acoustic matching layer *7a* extended to an area where the piezoelectric element 1 does not exist.

The manufacturing method and the operation of the ninth embodiment will not be described here since they are similar to those of eight embodiment. Further, the effect of the ninth embodiment will also not be described here since it is similar to that of the first embodiment.

Figure 16:
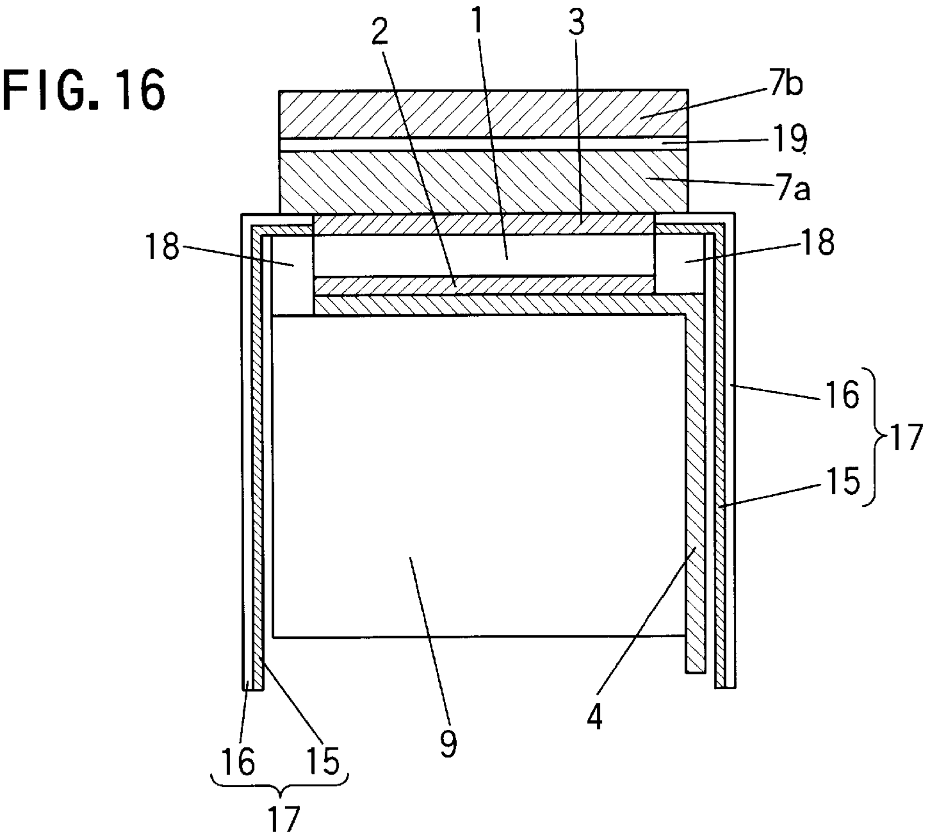
FIG. 16 is a schematic cross sectional view of an ultrasonic probe of a tenth embodiment according to the present invention.
Figure 17:
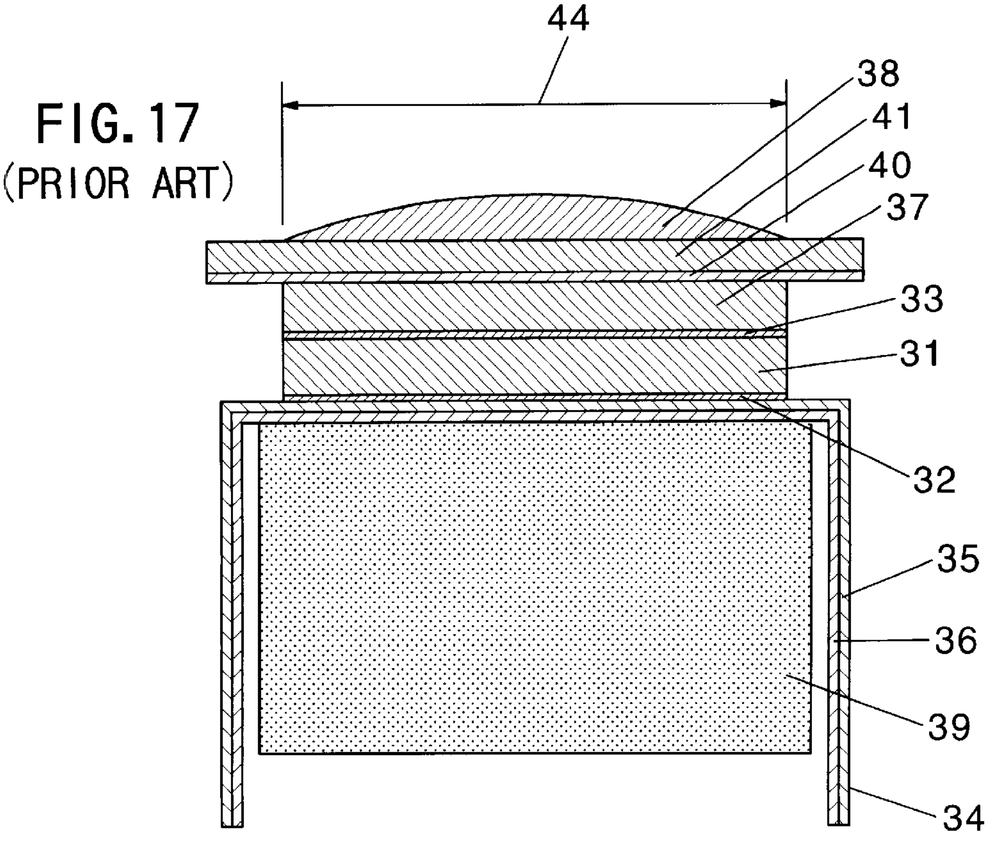
FIG. 17 (PRIOR ART)
FIG. 17 is a cross sectional view of an ultrasonic probe for a conventional ultrasonic diagnostic apparatus.
Figure 18:
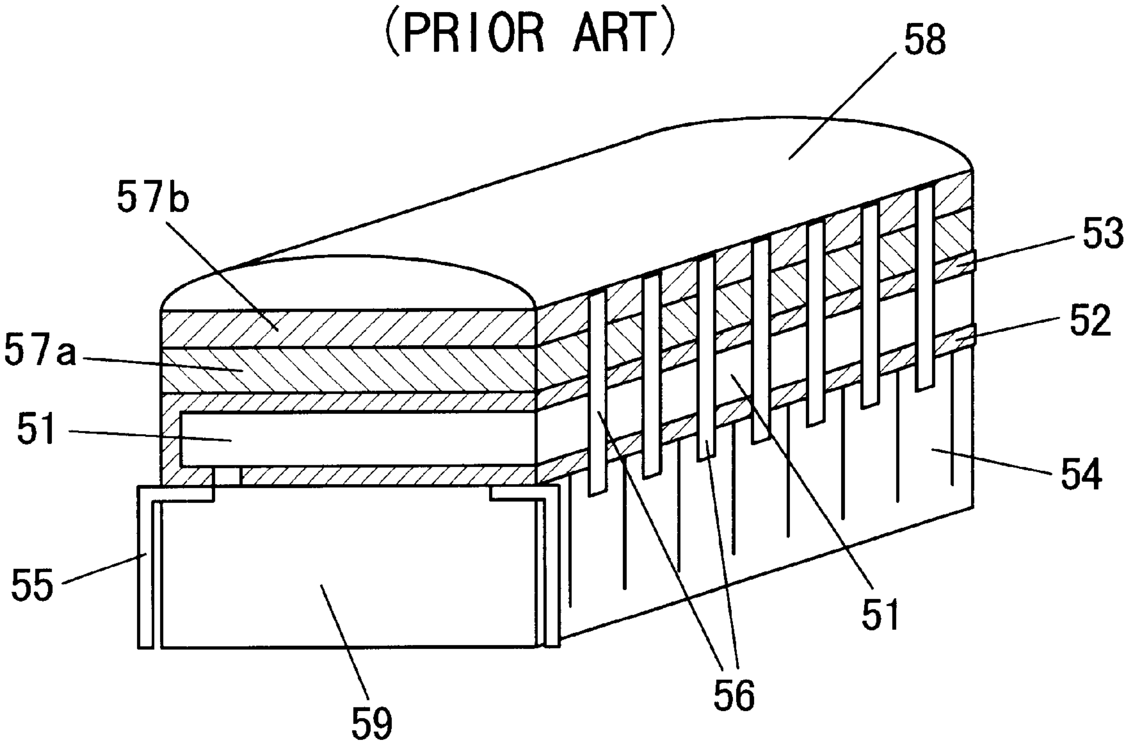
FIG. 18 (PRIOR ART)
FIG. 18 is a perspective view of an ultrasonic probe for a conventional ultrasonic diagnostic apparatus.

FIG. 16 shows an ultrasonic probe of the tenth embodiment according to the present invention. The tenth embodiment is different from the eighth and the ninth embodiment in that a conductive layer 19 electrically connected to the first acoustic matching layer *7a* is provided on the second acoustic matching layer *7b,* which is provided on an upper surface of the first acoustic matching layer *7a*. As for the components shown in FIG. 16, the piezoelectric element 1, the ground electrode 3, the positive electrode 2, the first acoustic matching layer *7a,* the conductive film 17, the FPC4, and the backing material 9 are similar to those of the eighth embodiment.

Referring to FIG. 16, the ground electrode 3 and the positive electrode 2 are provided on two opposite faces of the piezoelectric element 1, respectively. The first acoustic matching layer *7a* is provided on an upper surface of the piezoelectric element 1 for efficiently propagating an ultrasonic wave. The conductive film 17 composed of a base film 15 and a conductive copper layer 16 is disposed on each side of the piezoelectric element 1. At both side end portions of an under surface of the first acoustic matching layer *7a,* the conductive copper layer 16 of the conductive film 17 and the first acoustic matching layer *7a* are electrically connected to each other by a conductive adhesive.

The second acoustic matching layer *7b* is provided on an upper surface of the first acoustic matching layer *7a*. This second acoustic matching layer *7b* has a function to efficiently propagate the ultrasonic wave and is made of high molecular material such as epoxy resin, polyimide, polyethylene-terephthalate, poly-sulphon, polycarbonate, polyester, polystyrene, or poly-phenylene-sulphide. A conductive layer 19 electrically connected to the first acoustic matching layer *7a* is provided on an under surface of the second acoustic matching layer *7b*. Further, an acoustic lens (not shown) is attached on an upper surface of the second acoustic matching layer *7b* by an adhesive. This acoustic lens is made of such material as silicone rubber, urethane rubber, plastics or the like for focusing the ultrasonic wave and has a convex surface on the upper side thereof(on the side facing a subject to be examined).

Further, the positive electrode 2 is a signal electrode formed as a pattern on, for example, a high molecular material film and is electrically connected to the FPC 4 by a conductive adhesive. The backing material 9 is made of such material as ferrite-rubber, epoxy or urethane rubber mixed with micro-balloons for holding the piezoelectric element 1 and for absorbing undesired ultrasonic waves. Further, at each side of the piezoelectric element 1, an insulating layer 18 is provided in a space format between the first acoustic matching layer *7a* and the backing material 9. This insulating layer 18 is made of insulating material such as epoxy resin so as to insulate the conductive film 17 from the FPC 4 and the positive electrode 2, and also to support the first acoustic matching layer *7a* extending to an area where the piezoelectric element 1 does not exists.

According to the tenth embodiment, there is an advantageous effect in that, in addition to the effects realized by the eighth and the ninth embodiments, the second acoustic matching layer *7b* having the conductive layer 19 electrically connected to the first acoustic matching layer *7a* makes it possible to maintain an electrical connection even if the piezoelectric element 1 or the first acoustic matching layer 7*a* is cracked by an external mechanical impact, and thereby the ultrasonic probe is less likely to fail and a stable quality may be provided.

EFFECT OF THE INVENTION

According to the present invention, high molecular material is disposed between a piezoelectric element and an acoustic matching layer, and a conductive layer is provided on the piezoelectric element side surface of the high molecular material so as to be electrically extended therefrom as a GND of a signal line. According to the present invention, the high molecular material having a conductive layer electrically connected to a first acoustic matching layer is disposed between the first acoustic layer on one electrode surface of the piezoelectric element and the second acoustic matching layer, and the high molecular material has an acoustic impedance substantially equal to that of the second acoustic matching layer. According to the present invention, there is provided the piezoelectric element having two electrodes each disposed on one side of the piezoelectric element, the acoustic matching layer disposed on one side of one of the electrodes and the backing material disposed on one side of the other of the electrodes, wherein conductive material electrically connected to one of the electrodes is disposed between this electrode and the acoustic matching layer, high molecular material having conductive material is disposed also on the acoustic matching layer side, and the high molecular material has acoustic impedance substantially equal to that of the acoustic matching layer. By adopting this structure, the ultrasonic probe can be formed into a slim shape which is easy to operate without degrading performance such as sensitivity or frequency characteristics or the like. Further, a high quality ultrasonic probe can be obtained since this structure causes no electrical problem due to breakage of wire even if the piezoelectric element is cracked by a mechanical impact or the like.

Further, another advantageous effect of reducing noise can be obtained.

Further, an alternative ultrasonic probe of the present invention comprises the piezoelectric element having two electrodes disposed on each side thereof, the backing material on one electrode side of the piezoelectric element, and a signal electrical terminal disposed between the piezoelectric element and the backing material. The signal electrical terminal is composed of insulating material facing the backing material and conductive material facing one electrode and electrically connected to the piezoelectric element. The insulating material of the signal electrical terminal has a thickness smaller than 1/25 wavelength of the ultrasonic wave within the area facing the ultrasonic wave emitting face. This structure allows the ultrasonic probe to have a good sensitivity in transmitting and receiving the ultrasonic wave, a good resolution, and also a good frequency characteristic. Accordingly, a highly sensitive image with high resolution can be obtained in an ultrasonic diagnostic apparatus. Further, since the electrical connection can be maintained even if the piezoelectric element is cracked by mechanical impact or the like, an ultrasonic probe which is less likely to fail and has a stable quality can be obtained.

Further, another alternative ultrasonic probe of the present invention comprises the piezoelectric element having two electrodes disposed on each side thereof, the acoustic matching layer contacting one electrode, and the backing material disposed on the other side of the piezoelectric element. The acoustic matching layer is made of conductive material and is electrically connected to the one electrode. The end of the acoustic matching layer is electrically connected to the conductive film disposed on the side portion of the backing material. The one electrode is extended from the conductive film.

The structure described above allows the curved surface to be easily formed after dice machining, and further allows the electrical connection to be maintained through the conductive acoustic matching layer even if the piezoelectric element is cracked by external mechanical impact. Thus, the piezoelectric element performance is not deteriorated and the ultrasonic probe is less likely to fail, and thereby stable quality can be accomplished. Further, since the piezoelectric element need not to be exposed to a high temperature environment, an ultrasonic probe of the present invention can be easily manufactured without degrading the performance of the piezoelectric element.

What is claimed is:

1. An ultrasonic probe comprising:

a piezoelectric element having a first side and a second side;

a first electrode on said first side of said piezoelectric element;

a second electrode on said second side of said piezoelectric element;

a backing material positioned such that said second electrode is located between said backing material and said second side of said piezoelectric element;

an acoustic matching layer having an acoustic impedance;

a high molecular weight material layer between said first electrode and said acoustic matching layer, said high molecular weight material layer having an acoustic impedance that is substantially equal to said acoustic impedance of said acoustic matching layer; and a conductive layer electrically connected to said first electrode and positioned between said first electrode and said acoustic matching layer.

2. The ultrasonic probe according to claim 1, wherein a combined total thickness of said high molecular weight material layer and acoustic matching layer is substantially equal to a quarter wavelength of an ultrasonic wave to be transmitted by the ultrasonic probe.

3. The ultrasonic probe according to claim 1, wherein said high molecular weight material layer comprises a material selected from the group consisting of polyimide, polyethylene-terephthalate, poly-sulphon, polycarbonate, polyester, polystyrene and poly-phenylene-sulphide.

4. An ultrasonic probe comprising a piezoelectric element having a first side and a second side;

a first electrode on said first side of said piezoelectric element;

a second electrode on said second side of said piezoelectric element;

a backing material positioned such that said second electrode is located between said backing material and said second side of said piezoelectric element;

a first acoustic matching layer;

a second acoustic matching layer having an acoustic impedance;

a high molecular weight material layer between said first acoustic matching layer and said second acoustic matching layer, said high molecular weight material layer having an acoustic impedance that is substantially equal to said acoustic impedance of said second acoustic matching layer; and a conductive layer electrically connected to said first acoustic matching layer and positioned between said first acoustic matching layer and said second acoustic matching layer.

5. The ultrasonic probe according to claim 4, wherein a combined total thickness of said high molecular weight material layer and said second acoustic matching layer is substantially equal to a quarter wavelength of an ultrasonic wave to be transmitted by the ultrasonic probe.

6. The ultrasonic probe according to claim 4, wherein said high molecular weight material layer comprises a material selected from the group consisting of polyimide, polyethylene-terephthalate, poly-sulphon, polycarbonate, polyester, polystyrene and poly-phenylene-sulphide.

7. An ultrasonic probe comprising:

a piezoelectric element having a first side and a second side;

a first electrode on said first side of said piezoelectric element;

a second electrode on said second side of said piezoelectric element;

a backing material positioned such that said second electrode is located between said backing material and said second side of said piezoelectric element;

an acoustic matching layer having an acoustic impedance, a high molecular weight material layer between said first electrode and said acoustic matching layer, said high molecular weight material layer having an acoustic impedance that is substantially equal to said acoustic impedance of said acoustic matching layer;

a first conductive layer electrically connected to said first electrode and positioned between said first electrode and said acoustic matching layer; and a second conductive layer positioned between said first electrode and said acoustic matching layer.

8. The ultrasonic probe according to claim 7, wherein said second conductive layer is positioned between said high molecular weight material layer and said acoustic matching layer and is to function as a shield electrode.

9. An ultrasonic probe comprising:

a piezoelectric element having a first face and a second face;

a backing material on said second face of said piezoelectric element;

a first acoustic matching layer on said first face of said piezoelectric element, said first acoustic matching layer having an acoustic impedance;

a second acoustic matching layer having an acoustic impedance;

a high molecular weight material layer between said first acoustic matching layer and said second acoustic matching layer, said high molecular weight material layer having an acoustic impedance that is (i) between said acoustic impedance of said first acoustic matching layer and said acoustic impedance of said second acoustic matching layer, (ii) substantially equal to said acoustic impedance of said second acoustic matching layer, or (iii) substantially equal to said acoustic impedance of said first acoustic matching layer; and a conductive layer between said first acoustic matching layer and said second acoustic matching layer.

10. An ultrasonic probe comprising:

a piezoelectric element having a first side and a second side;

a first electrode on said first side of said piezoelectric element;

a second electrode on said second side of said piezoelectric element;

a backing material positioned such that said second electrode is located between said backing material and said second side of said piezoelectric element; and a signal electrical terminal between said backing material and said second side of said piezoelectric element, said signal electrical terminal including an insulator facing said backing material and a conductive material facing said second electrode, with said conductive material being electrically connected to said piezoelectric element, wherein said insulator has a thickness of at most 1/25 of a wavelength of an ultrasonic wave to be transmitted by the ultrasonic probe.

11. The ultrasonic probe according to claim 10, wherein said insulator comprises a material selected from the group consisting of polyimide, polyethylene-terephthalate, polysulphon, polycarbonate, polyester, polystyrene and poly-phenylene-sulphide.

12. An ultrasonic probe comprising:

a piezoelectric element having a first side and a second side;

a first electrode on said first side of said piezoelectric element;

a second electrode on said second side of said piezoelectric element;

a backing material positioned such that said second electrode is located between said backing material and said second side of said piezoelectric element;

a first signal electrical terminal between said backing material and said second side of said piezoelectric element, said first signal electrical terminal including an insulator facing said backing material and a conductive material facing said second electrode, with said conductive material being electrically connected to said piezoelectric element; and a second signal electrical terminal on a lateral side of said backing material said second signal electrical terminal including an insulator and a conductive material, with said conductive material of said second signal electrical terminal being electrically connected to said conductive material of said first signal electrical terminal, where said insulator of said first signal electrical terminal has a thickness of at most 1/25 of a wavelength of an ultrasonic wave to be transmitted by the ultrasonic probe.

13. The ultrasonic probe according to claim 12, wherein said insulator of said first signal electrical terminal comprises a material selected from the group consisting of polyimide, polyethylene-terephthalate, poly-sulphon, polycarbonate, polyester, polystyrene and poly-phenylene-sulphide.

14. An ultrasonic probe comprising:

a piezoelectric element having a first side and a second side;

a positive electrode on said first side of said piezoelectric element;

a ground electrode on said second side of said piezoelectric element; and a conductive layer at least partially overlapping at least one of said positive electrode and said ground electrode, said conductive layer having a thickness at least in an acoustic effective area that is less than a thickness of said conductive layer outside of the acoustic effective area.

15. The ultrasonic probe according to claim 14, further comprising a base material layer on which is located said conductive layer.

16. An ultrasonic probe comprising:

a piezoelectric element having a first side and a second side;

a positive electrode on said first side of said piezoelectric element;

a ground electrode on said second side of said piezoelectric element;

an acoustic matching layer on said ground electrode;

a base material layer over said acoustic matching layer; and a conductive layer on said base material layer, said conductive layer having a thickness at least in an acoustic effective area that is less than a thickness of said conductive layer outside of the acoustic effective area.

17. An ultrasonic probe comprising:

a piezoelectric element having a first side and a second side;

a first electrode on said first side of said piezoelectric element;

a second electrode on said second side of said piezoelectric element;

a backing material positioned such that said second electrode is located between said backing material and said second side of said piezoelectric element;

a conductive acoustic matching layer contacting and being electrically connected to said first electrode;

an insulating layer on side of said piezoelectric element and between an end portion of said conductive acoustic matching layer and an end portion of said backing material, said insulating layer being made of a material selected from the group consisting of ceramic, acrylic resin, plastic, epoxy resin, cyanoacrylate and urethane resin; and a flexible conductive film on a side portion of said backing material, wherein said end portion of said conductive acoustic matching layer is electrically connected to said flexible conductive film and said first electrode extends to said flexible conductive film.

18. An ultrasonic probe comprising:

a piezoelectric element having a first side and a second side;

a first electrode on said first side of said piezoelectric element;

a second electrode on said second side of said piezoelectric element;

a backing material positioned such that said said second electrode is located between said backing material and said second side of said piezoelectric element;

a conductive acoustic matching layer contacting and being electrically connected to said first electrode;

an acoustic matching layer on said conductive acoustic matching layer;

an insulating layer on a side of said piezoelectric element and between an end portion of said conductive acoustic matching layer and an end portion of said backing material, said insulating layer being made of a material selected from the group consisting of ceramic, acrylic resin, plastic, epoxy resin, cyanoactylate and urethane resin; and a flexible conductive film on a side portion of said backing material, wherein said end portion of said conductive acoustic matching layer is electrically connected to said flexible conductive film and said first electrode extends to said flexible conductive film.

* * * * *